(12) United States Patent
Morin et al.

(10) Patent No.: US 10,495,628 B2
(45) Date of Patent: *Dec. 3, 2019

(54) MULTIPLEXED BIOMARKER QUANTITATION BY NANOPORE ANALYSIS OF BIOMARKER-POLYMER COMPLEXES

(71) Applicant: Ontera Inc., Santa Cruz, CA (US)

(72) Inventors: Trevor J. Morin, Santa Cruz, CA (US); Daniel Alexander Heller, Santa Cruz, CA (US); William B. Dunbar, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,632

(22) Filed: Jul. 8, 2018

(65) Prior Publication Data
US 2018/0335418 A1 Nov. 22, 2018

Related U.S. Application Data

(63) Continuation of application No. 14/315,269, filed on Jun. 25, 2014, now Pat. No. 10,048,245.

(60) Provisional application No. 61/839,328, filed on Jun. 25, 2013.

(51) Int. Cl.
*G01N 33/487* (2006.01)
*G01N 33/68* (2006.01)

(52) U.S. Cl.
CPC .............................. *G01N 33/48721* (2013.01)

(58) Field of Classification Search
CPC .......................... G01N 33/487; G01N 33/447
See application file for complete search history.

(56) References Cited

U.S. PATENT DOCUMENTS

| | | | |
|---|---|---|---|
| 5,641,630 A | 6/1997 | Snitman et al. | |
| 5,843,653 A | 12/1998 | Gold et al. | |
| 2004/0224336 A1 | 11/2004 | Wagner | |
| 2005/0026202 A1 | 2/2005 | Edman et al. | |
| 2007/0048759 A1 | 3/2007 | Luo et al. | |
| 2007/0190543 A1 | 8/2007 | Livak | |
| 2008/0300142 A1 | 12/2008 | Getts et al. | |
| 2009/0050492 A1 | 2/2009 | Alocilja et al. | |
| 2010/0035260 A1 | 2/2010 | Olasagasti et al. | |
| 2011/0108423 A1 | 5/2011 | Van Der Zaag et al. | |
| 2012/0276530 A1* | 11/2012 | Meller ................ | C12Q 1/6839 435/6.11 |
| 2013/0180867 A1* | 7/2013 | Rosenstein ......... | G01N 33/48721 205/777.5 |
| 2013/0233709 A1 | 9/2013 | Dunbar et al. | |
| 2014/0087390 A1* | 3/2014 | Oliver ................ | G01N 33/5308 435/6.19 |

FOREIGN PATENT DOCUMENTS

| | | |
|---|---|---|
| WO | WO 2012/009578 A2 | 1/2012 |
| WO | WO 2012/116161 A1 | 8/2012 |
| WO | WO 2013/012881 A2 | 1/2013 |

OTHER PUBLICATIONS

Bell, C., "Structure and Mechanism of *Escherichia coli* RecA ATPase," Molecular Microbiology, Jan. 2005, pp. 358-366, vol. 58, No. 2.
Extended European Search Report for European Patent Application No. EP 14818118.3, dated Oct. 17, 2016, 8 Pages.
Hall, A.R. et al., "Hybrid Pore Formation by Directed Insertion of a-Haemolysin into Solid-State Nanopores," Nature Nanotechnology, Nov. 28, 2010, vol. 5, No. 12. pp. 874-877.
Haque, F. et al., "Solid-State and Biological Nanopore for Real-Time Sensing of Single Chemical and Sequencing DNA," Nano Today, 2013, vol. 8, No. 1, pp. 56-74.
Howorka, S. et al., "Nanopore Analytics: Sensing of Single Molecules," Chemical Society Reviews, 2009, vol. 38, No. 8, pp. 2360-2384.
Kowalczyk, S. et al., "Modeling the conductance and DNA blockade of solid-state nanopores," Nanotechnology, 2011, vol. 22, pp. 1-5.
Kowalczyk, S. W. et al., "Detection of Local Protein Structures Along DNA Using Solid-State Nanopores," Nano Letters, 2010, vol. 10, No. 1, pp. 324-328.
Miles, B.N. et al., "Single Molecule Sensing With Solid-State Nanopores: Novel Materials, Methods, and Applications," Chemical Society Reviews, 2013, vol. 42, No. 1, pp. 15-28.
PCT International Search Report and Written Opinion, PCT Application No. PCT/US2014/044185, dated Oct. 17, 2014, 16 paqes.
Rajan, R. et al., "Probing the DNA sequence specificrty of *Eschelichia coli* RECA protein," Nucleic Acids Research, 2006, vol. 34, No. 8, pp. 2463-2471.
Reiner, J.E. et al., "Disease Detection and Management Via Single Nanopore-Based Sensors," Chemical Review, 2012, vol. 112, No. 12, pp. 6431-6451.
Shim, J. et al., "Detection and Quantification of Methylation in DNA Using Solid-State Nanopores," Scientific Reports, 2013, vol. 3, pp. 1-8.

(Continued)

*Primary Examiner* — Amy M Bunker
(74) *Attorney, Agent, or Firm* — Fenwick & West LLP

(57) ABSTRACT

Devices and methods for detecting a target molecule are provided herein. The methods entail contacting a sample with a polymer scaffold, the polymer comprising at least one association site configured to associate with the target molecule. The sample is brought into contact with the polymer to determine whether the target molecule is present in the sample under conditions allowing the target molecule, if present, to associate with the polymer scaffold. The methods further involve loading the polymer into a device comprising a pore or channel that connects two volumes, configuring the device to pass the polymer through the pore or channel from one volume to the other volume, and determining, with a sensor configured to detect objects passing through the pore or channel, whether the target molecule is associated with the association site, and thereby detecting the presence or absence of the target molecule in the sample.

8 Claims, 15 Drawing Sheets

(56) References Cited

OTHER PUBLICATIONS

Singer, A. et al. "Electronic Barcoding of a Viral Gene at the Single-Molecule Level," Nano Letters, 2012, vol. 12, No. 3, pp. 1722-1728.
Smeets, R. M. M. et al., "Translocation of RecA-Coated Double-Stranded DNA Through Solid-State Nanopores," Nano Letters, 2008, vol. 9, No. 9, pp. 3089-3095.
Yildiz, F.H. et al., "VpsR, a Member of the Response Regulators of the Two-Component Regulatory Systems, Is Required for Expression of vps Biosynthesis Genes and EPSET-Associated Phenotypes in Vibrio cholerae 01 El Tor," Journal of Bacteriology, 2001, pp. 1716-1726, vol. 183, No. 5.
United States Office Action, U.S. Appl. No. 14/315,269, dated Jan. 20, 2016, 23 pages.
United States Office Action, U.S. Appl. No. 14/315,269, dated Mar. 27, 2017, 34 pages.
United States Office Action, U.S. Appl. No. 14/315,269, dated May 7, 2015, 24 pages.
United States Office Action, U.S. Appl. No. 14/315,269, dated May 31, 2016, 31 pages.
United States Office Action, U.S. Appl. No. 14/315,269, dated Nov. 28, 2016, 38 pages.
United States Office Action, U.S. Appl. No. 14/315,269, dated Sep. 28, 2017, 20 pages.

* cited by examiner

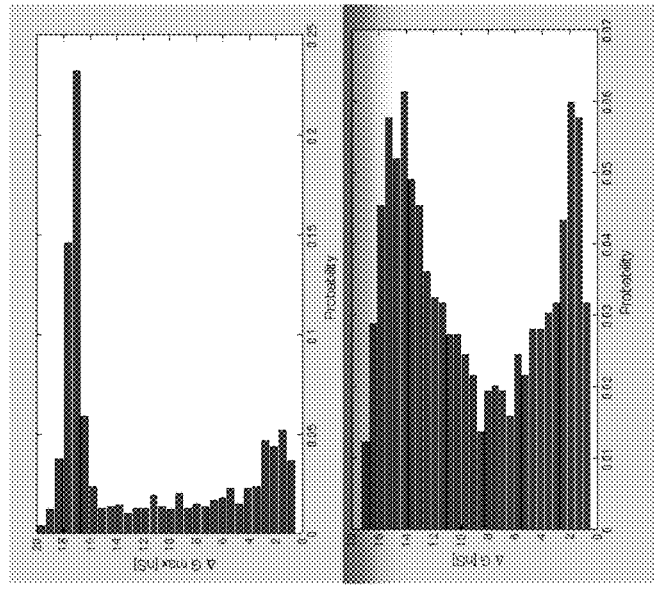
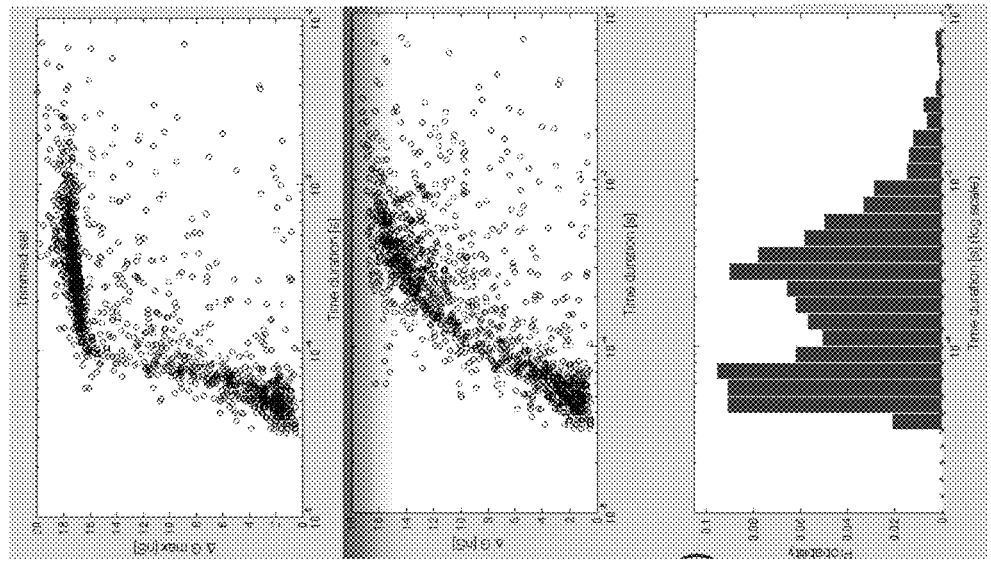
FIG. 12A  FIG. 12B  FIG. 12C  FIG. 12D  FIG. 12E

MULTIPLEXED BIOMARKER QUANTITATION BY NANOPORE ANALYSIS OF BIOMARKER-POLYMER COMPLEXES

CROSS REFERENCE TO RELATED APPLICATIONS

This application is a continuation of U.S. application Ser. No. 14/315,269, filed Jun. 25, 2014, now U.S. Pat. No. 10,048,245, which claims the benefit under 35 U.S.C. § 119(e) of U.S. Provisional Application Ser. No. 61/839,328 filed Jun. 25, 2013, each of which is incorporated in its entirety by reference.

BACKGROUND

Detection of nano-scale and micro-scale particles, such as DNA, RNA, proteins, or other molecular markers released by circulating tumor cells, bacteria, or viruses, has immense clinical utility. For example, such detection allows for the detection of pathogens, the diagnosis of diseases, and the personalization of medical treatments and health programs. Such detection can also facilitate the search for effective pharmaceutical drug compounds and biotherapeutics. Detection of nano-scale and micro-scale particles, may also allow clinicians to identify abnormal hormones, ions, elements, carbohydrates, proteins, or other molecules produced by a patient's body and/or identify the presence of poisons, illegal drugs, or other harmful chemicals ingested or injected into a patient.

Currently, an array of techniques are used for molecular detection and quantitation. For example, nucleotide sequences may be detected using complementary probes or primers in conjunction with devices designed to detect bound probes or primers. Such techniques typically require hybridization and/or amplification of the nucleotides. As another example, a protein is commonly detected with an enzyme-linked immune-sorbent assay (ELISA) device and an antibody that specifically binds to the protein. Available techniques for molecular detection are generally expensive, labor-intensive, skill-intensive, and/or time-intensive. A need exists for improved molecular detection techniques, which produce accurate results quickly, cheaply, and easily.

SUMMARY

Various aspects disclosed herein may fulfill one or more of the above-mentioned needs. The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for improved anastomosis devices and methods.

One aspect of the present disclosure is directed to a method for determining whether a target molecule is present in a sample. In various embodiments, the method includes: (a) contacting a sample with a polymer scaffold, the polymer scaffold comprising at least one association site configured to associate with a target molecule; (b) loading the polymer scaffold into a device comprising a pore or channel that connects two volumes, and configuring the device to pass the polymer scaffold through the pore or channel from one volume to the other volume; and (c) determining, with a sensor configured to detect objects passing through the pore or channel, whether the target molecule is associated with the polymer scaffold at the association site, wherein association of the target molecule to the polymer scaffold at the association site indicates the presence of the target molecule in the sample.

In at least some embodiments of the method, the target molecule is selected from the group consisting of a protein, a peptide, a nucleic acid, a metabolite, a sugar, a vitamin, a chemical compound, an ion, and an element. Additionally or alternatively, the target molecule may be an antibody, an epitope, a hormone, a neurotransmitter, a cytokine, a growth factor, a cell recognition molecule, and/or a receptor.

In some embodiments, step (a) is performed prior to step (b). In other embodiments, step (b) is performed prior to step (a).

In some embodiments, the method further includes changing a condition suspected of altering the association of the target molecule to the polymer, and carrying out the determination again. In some such embodiments, changing the condition is selected from the group consisting of: removing the target molecule from the sample; adding an agent that competes or assists with association of the target molecule to the association site; and changing the pH, salt concentration, or temperature.

In some embodiments, the association site comprises a chemical modification on the polymer for binding the target. In some aspects, the chemical modification is selected from the group consisting of biotinylation, acetylation, methylation, summolation, glycosylation, phosphorylation, and oxidation.

In at least some embodiments, the polymer is formed of deoxyribonucleic acid (DNA), a ribonucleic acid (RNA), a peptide nucleic acid (PNA), a DNA/RNA hybrid, a polypeptide, or a chemically derived polymer. In at least some embodiments, the polymer is chemically modified or synthesized.

In some embodiments, the association between the polymer and the target molecules includes one or more of a covalent bond, a hydrogen bond, an ionic bond, a metallic bond, van der Walls force, hydrophobic interaction, cation-pi, and/or a planar stacking interaction.

In some embodiments, the method further comprises contacting the sample with a molecule capable of associating with the target molecule.

In some embodiments, the polymer comprises only one association site. In other embodiments, the polymer includes at least two association sites, each association site configured to associate with the same target molecule. In still other embodiments, the polymer includes at least two different association sites, each of the different association sites configured to associate with a different target molecule. In such embodiments, the sensor is configured to identify whether each association site has a target bound thereto.

In some embodiments, the sensor comprises electrodes further configured to generate a voltage across the two volumes.

In at least some embodiments, the device comprises an upper chamber, a middle chamber and a lower chamber, wherein the upper chamber is in communication with the middle chamber through a first pore, and the middle chamber is in communication with the lower chamber through a second pore. In such embodiments, the device provides a first voltage between the upper chamber and the middle chamber and provides a second voltage between the middle chamber and the lower chamber, each voltage being independently adjustable such that a net voltage differential between the first and second voltages is present across the upper and lower chambers, and the first pore and second pore are about 1 nm to about 100 nm in diameter so as to pass a single charged polymer containing monomer units therethrough. In such embodiments, the rate of passage of the single charged polymer controlled by the net voltage differential.

In some embodiments, the method further comprises moving the polymer in a reverse direction after the association site passes through the pore, so as to identify, again, whether the target is associated with the association site on the polymer.

In some embodiments, the method further comprises moving the polymer through two nanopores for dual-nanopore control and measurement, to improve detection and mapping of one or more target molecules on the polymer.

An additional aspect of the present disclosure is directed to kits, packages or mixtures for detecting the presence of a target molecule. In various embodiments, the kit, package or mixture includes: a polymer scaffold comprising at least one association site configured to associate with a target, and a device comprising a pore or channel forming an opening within a structure that separates an interior space of the device into two volumes. The device is configured to allow the polymer to pass through the pore or channel from one volume to the other volume, and the device further comprises a sensor configured to identify, as the polymer passes through the pore, whether the target is associated with the polymer.

In at least some embodiments, the kit, package or mixture further comprises a control molecule configured to bind to the polymer scaffold at a specific location. The kit, package or mixture may additionally or alternatively further include a sample suspected of containing the target molecule. Such a sample may further comprise a detectable label capable of binding to the target molecule.

BRIEF DESCRIPTION OF THE DRAWINGS

The above-mentioned aspects, as well as other features, aspects, and advantages of the present technology will now be described in connection with various embodiments, with reference to the accompanying drawings.

FIGS. 3A and 3B depict examples of current profiles detected using one embodiment of the nanopore device disclosed herein. The figures further show a schematic of the molecules causing changes in the detected current profile. Specifically, FIG. 3A shows current profiles consistent with higher salt concentrations (>0.4 M KCl, for example at 1M KCl) in the experimental buffer. In the experiment represented by current profiles, current attenuation is a relatively shallow level (302) with unbound DNA (304) passing through the pore. The current may also have at least one deeper blockade level different than the unbound DNA level (303) to signal target-bound DNA (305) passing through the pore. By contrast, FIG. 3B shows current profiles consistent with lower salt concentrations (<0.4 M KCl, for example at 100 mM KCl) in the experimental buffer. In that case, current enhancement is at one level (306) with unbound DNA (307) passing through the pore, but may have at least one blockade level with the opposite polarity than the unbound DNA level (308) to signal target-bound DNA (309) passing through the pore.

Specifically, FIG. 4A depicts a schematic diagram of a nanopore device, comprising a photograph of a top view of a nanopore device and a schematic of the voltage and voltage source applied across the pore.

FIG. 4B depicts a representative current trace showing a blockade event resulting from the passage of a polymer through the pore.

FIG. 4C depicts a scatter plot showing translocation time vs. change in current of the blockade events recorded over 16 minutes.

Specifically, FIG. 5A is a schematic of a dual-pore chip and a dual-amplifier electronics configuration for independent voltage control ($V_1$, $V_2$) and current measurement ($I_1$, $I_2$) of each pore. Three chambers, A-C, are shown and are volumetrically separated except by common pores. Feasible chip parameters are, for example, an inter-pore distance 10-500 nm, membrane thickness 0.3-50 nm, and pore diameters 1-100 nm.

FIG. 5B is a schematic where electrically, $V_1$ and $V_2$ can principally cross each nanopore resistance, by constructing a device that minimizes all access resistances to effectively decouple $I_1$ and $I_2$.

FIG. 5C is another schematic of a dual-pore chip. In FIG. 5C, competing voltages are used for control, with blue arrows showing the direction of each voltage force. Assuming pores with identical voltage-force influence and using $|V_1|=|V_2|+\sigma V$, the value $\sigma V>0(<0)$ is adjusted for tunable motion in the $V_1(V_2)$ direction. In practice, although the voltage-induced force at each pore will not be identical with $V_1=V_2$, calibration experiments can identify the required voltage bias that will result in equal pulling forces, for a given two-pore chip, and variations around that bias can then be used for directional control.

FIG. 7 shows a 5,631 bp dsDNA scaffold and the location of 10 total VspR binding sites. Of the 10 VspR binding sites, 5 are of one 14 base-pair sequence, 3 of a different 18 base pair sequence, and 2 are of a 27 base pair sequence. Also shown are the distances (in base pairs) between the binding sites.

FIG. 8A shows a graphic depicting a 5,631 bp dsDNA scaffold passing through the pore, and a representative current enhancement event (downward 50 pA shift lasting 100 microseconds) when the scaffold passes through the pore. FIG. 8B) shows a graphic depicting multiple VspR bound to a dsDNA scaffold that is passing through the pore, and a representative current attenuation event (upward 150 pA shift lasting 1.1 milliseconds) when the VspR-bound scaffold passes through the pore. At an applied voltage of −100 mV, the open channel current is negative, so downward events correspond to current enhancement events, and upward events correspond to current attenuation events. The shift direction is preserved, even though the baseline is zeroed for display purposes.

FIGS. 12A-12E shows scatter plots and histograms depicting all 1385 events recorded over 10 minutes in one experiment conducted using embodiments of methods described herein. In the depicted graphs, one data point is provided for each event. In particular, the depicted graphs show: FIG. 12A maximum conductance in nS (maximum current shift in pA divided by voltage in mV) vs. time duration in seconds, with time duration on a log-scale; FIG. 12B a probability histogram of the maximum conductance shift values; FIG. 12C mean conductance (mean current shift divided by voltage) vs. time duration, with time duration on a log-scale; FIG. 12D a probability histogram of the mean conductance values; and FIG. 12E a probability histogram of the time duration on a log-scale.

Specifically, FIG. 13A is gel shift assay. Specifically, the DNA/RecA/mAb ARM191 Gel Shift Experiments (EMSA) have lanes: 1) Ladder, top rung 5000 bp; 2) Scaffold DNA only in RecA labeling buffer; 3) DNA/RecA complex, 1:1 RecA protein to theoretical RecA binding sites; 4) DNA/ RecA/Ab complex, DNA/Rec incubated with a 1:2000 dilution of monoclonal Ab ARM191; 5) Scaffold DNA only in Ab labeling buffer; and 6) Scaffold DNA mixed with mAb (ARM191).

FIG. 13B shows representative events for DNA (230 pA, 0.1 ms), DNA/RecA (390 pA, 1.1 ms), and probable DNA/RecA/Ab (860 pA, 1.5 ms). RecA-bound DNA event amplitudes are uniformly smaller than in earlier figures (FIGS. 10, 11, 12A-12E) since the pore used to measure these events is considerably larger (27-29 nm in diameter).

FIG. 13C, depicts: a (i) Scatter plot of Δl vs. tD and (ii) horizontal probability histogram of Δl for two separate, overlaid experiments. In a RecA alone control experiment, 0.5 uM RecA (*) was measured at 180 mV in 1M KCl with a 20 nm diameter pore, generating 767 events over 10 min. Note that only 0.6% of RecA events exceed a criteria of (600 pA, 0.2 ms) under these conditions. In another experiment, three reagents were added in sequence in 1M LiCl. First, 0.1 uM DNA (□) was measured at 200 mV with a 20 nm diameter pore, generating 402 events at 0.1 events/sec. After the pore enlarged to 27 nm, 1.25 nM DNA/RecA ( ) was added, generating 3387 events at 1.44 events/sec. Lastly, 1.25 nM DNA/RecA/Ab (O) was added generating 4953 events at 4.49 events/sec. Events exceeding the (600 pA, 0.2 ms) criteria grew monotonically from 0% with DNA alone, to 5.2% (176) with DNA/RecA added, and up to 9.8% (485) with DNA/RecA/Ab added. While RecA could have increased event durations in LiCl, as shown for DNA, event amplitudes are unlikely to shift significantly toward the (600 pA, 0.2 ms) criteria.

Figure 1:
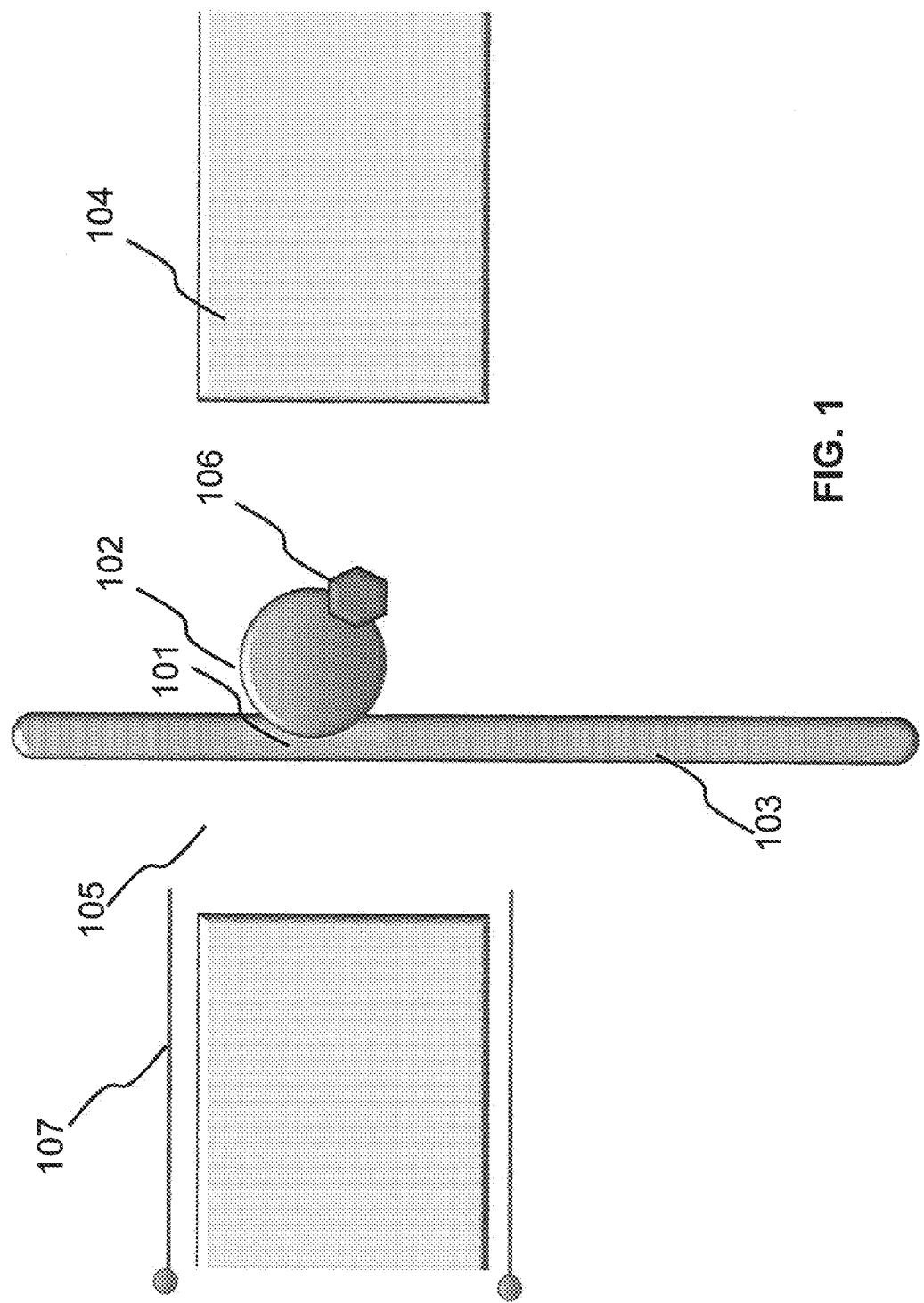
FIG. 1 illustrates a schematic diagram of one embodiment of a nanopore device with a polymer scaffold and target molecule extending through a pore of the device. It further helps illustrates one embodiment of a method for detection of a target molecule on the polymer scaffold.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a", "an" and "the" include plural references unless the context clearly dictates otherwise. For example, the term "an electrode" includes a plurality of electrodes, including mixtures thereof. While some embodiments may be described as including "at least two," "more than one," or "a plurality," the absence of such terms should not be interpreted as limiting a term to its singular form.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary and that equivalents of such are known in the art.

Molecular Detection

The present disclosure provides methods and systems for molecular detection and quantitation. In addition, the methods and systems can also be configured to measure the affinity of a molecule associating to a distinct site on the scaffold. Further, such detection, quantitation, and measurement can be carried out in a multiplexed manner, greatly increasing its efficiency.

Single nanopore devices have been used previously to detect modifications to dsDNA. To detect DNA modifications, probe molecules were chosen and added to a solution containing the dsDNA. These probe molecules bind specifically to particular modified DNA segments and are thus used to make known the presence of particular modified DNA segments. In one study, PNA probe molecules were shown to bind to specific sites on a dsDNA scaffold (Singer et al. Electronic barcoding of a viral gene at the single-molecule level. Nano Lett. (2012) vol. 12 (3) pp. 1722-8), and a single 3.7 nm diameter solid-state nanopore was used to detect the presence of one or two probes at chosen sites spaced 100-1000 bp apart. In another study, the protein MBD1 acted as the probe to detect methylated cytosine sites on an 800 bp dsDNA (Shim et al. Detection and quantification of methylation in DNA using solid-state nanopores. Scientific Reports (2013) vol. 3 pp. 1389). In these works, and others, the target of interest is the modified DNA site.

By contrast, the inventions described herein aim to detect target molecules within a sample. In various embodiments, a polymer scaffold is purposefully engineered or selectively chosen to contain sites along its length, which will bind to the target molecules to facilitate such detection.

FIG. 1 provides an illustration of one embodiment of the disclosed methods and systems. More specifically, the depicted system includes a target molecule 102 that is desired to be detected or quantitated. The depicted system also includes a polymer scaffold 103 configured to include at least one association site 101. The target molecule is capable of associating with (e.g., binding to) a specific association site 101 on the polymer scaffold 103. As described in more detail below, the polymer scaffold 103 may include chemical modifications or be chemically synthesized to achieve a structure that facilitates the association of the particular target molecule 102 to the association site 101.

Therefore, if present in a solution, the target molecule 102 associates with the polymer scaffold (or simply, "polymer") 103 at the specific association site 101. Such association causes the formation of a complex that includes the polymer 103 and the target molecule 102.

The formed complex can be detected using a nanopore device 104. As used herein, a nanopore device (or simply, "device") 104 includes a nanopore (or simply, "pore") 105 and a sensor 107. The pore 105 is a nano-scale opening in a structure (e.g., a membrane or substrate) separating two volumes. The sensor is configured to identify objects passing through the pore. For example, in some embodiments, the sensor identifies objects passing through the pore 105 by detecting a change in a measurable parameter, wherein the change is indicative of an object passing through the pore 105. The sensor may be positioned within or adjacent to the pore 105 or elsewhere within the two volumes. In some embodiments, the nanopore device 104 includes means, such as electrodes connected to power sources, for moving the polymer from one volume to another, across the pore 105. As the polymer 103 can be charged or be modified to contain charges, one example of such means generates a potential or voltage across the pore to facilitate and control the movement of the polymer 103. In a preferred embodiment, the sensor 107 comprises the electrodes, which are configured to both detect the passage of objects, and provide a voltage, across the pore 105.

When a sample that includes the formed complex is loaded in the nanopore device 104, the nanopore device 104 can be configured to pass the polymer 103 through the pore 105. When the association site 101 with target 102 is within the pore or adjacent to the pore 105, the association status can be detected by the sensor 107.

Figure 3A:
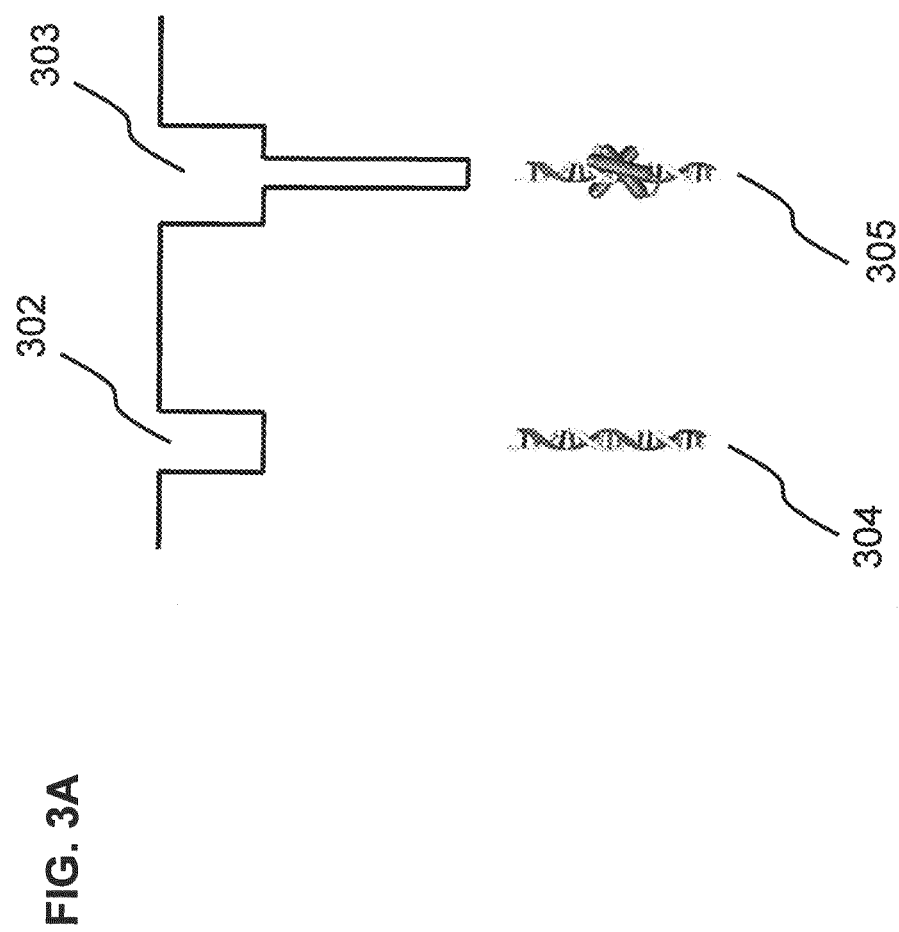
FIGS. 3A and 3B demonstrate that association of the target molecule to the scaffold can be detected, since it has a different current profile compared to DNA alone, when passing through a nanopore. In particular.

The "association status", as used herein, refers to whether the association site is occupied by a target molecule. Essentially, the association status can be one of two potential statuses: (i) the association site is free and not occupied by a target molecule (see 302 and 304 in FIG. 3A), or (ii) the association site is occupied by a target molecule, (see 303 and 305 in FIG. 3A). When the association site is occupied, the diameter of the polymer-target complex at the location of the association site is greater than the diameter of the polymer at locations that do not include an associated target molecule.

Detection of the association status of an association site can be carried out by various methods. In one aspect, by virtue of the different sizes of the association site at each status (i.e., occupied or unoccupied), when the association site passes through the pore, the different sizes result in different currents across the pore. In this respect, no separate sensor is required for the detection, as the electrodes, which are connected to a power source and can detect the current, can serve the sensing function. Either or both the electrodes, therefore, serve as a "sensor."

In some aspects, a molecule 106 is added to the complex to improve detection. This molecule is capable of associating with (e.g., binding to) the target molecule. In one aspect, the molecule includes a charge, either negative or positive, to facilitate detection. In another aspect, the molecule adds size to facilitate detection. In another aspect, the molecule includes a detectable label, such as a fluorophore.

In this context, an identification of status (ii) indicates that a molecule-target-polymer complex has formed. In this way, the target molecule is detected.

Polymer Scaffold

The polymeric scaffold of the present disclosure is designed to enable quantitation of one or more biomarkers (i.e., target molecules) that may be present in a solution. To this end, the scaffold should have one or more of several advantageous features that facilitate the association and/or detection of the target molecule-polymer complex. The scaffold may be synthetically fabricated, chemically modified, or specifically selected in order to incorporate one or more of the features into the scaffold. One advantageous feature incorporated into various scaffold designs is that the polymeric region between target association sites inhibits non-specific association of molecules in the sample. This can be done by randomizing the sequence of monomers forming the polymeric scaffold region between target association sites, as one example. Another feature is that the association sites are sufficiently far apart to enable detection of associated targets as the scaffold moves through a nanopore. In one example of a polymer having such a feature, the polymer includes 100 basepairs between association sites, and is designed for passage through a nanopore that is 10 nanometers in length. The range of distances for which target detection is possible is determined by the length of pores, speed of the polymer through the pore, bandwidth of the instrument, and whether more than one pore is used for measurement.

In various embodiments, the polymer scaffold is designed to have a particular number of particularly spaced association sites, and each association site is particularly structured to bind to a desired target molecule. For example, the association site may be formed of a sequence of identical monomer units, or selected or fabricated to have a particular conformation, i.e., three dimensional shape.

Non-limiting examples of polymers include nuclei acids such as deoxyribonucleic acid (DNA), ribonucleic acid (RNA), DNA/RNA hybrids, or peptide nucleic acid (PNA), and linearized proteins or peptides, or dendrimers. A DNA or RNA can be single-stranded or double-stranded, or can take on a desired secondary structure comprising both double stranded and single stranded structure.

In one aspect, the polymer is synthetic or chemically produced/synthesized by one or more steps of chemical coupling from monomer or precursor molecules.

In one aspect, the polymer is synthetic or chemically modified. Chemical modification can help stabilize the polymer, add charges to the polymer to increase mobility, maintain linearity, or add or modify binding specificity. In some aspects, the chemical modification is biotinylation, acetylation, methylation, summolation, oxidation, phosphorylation, or glycosylation. In some embodiments, the chemical modification includes the addition or incorporation of polyethylene glycol, non-native amino acids, and/or biotin into the polymer scaffold.

In some aspects, the polymer is charged. DNA, RNA, PNA and proteins are typically charged under physiological conditions. Such polymers can be further modified to increase or decrease charge. Other polymers can be modified to introduce charges. Charges on the polymer can be useful for driving the polymer to pass through the pore of a nanopore device. For instance, a charged polymer can move across the pore by virtue of an application of voltage across the pore.

In some aspects, when charges are introduced to the polymer, the charges can be added at the ends of the polymer. In some aspects, the charges are spread over the polymer. The added charge may be in the form of dsDNA, ssDNA, dsRNA or ssRNA.

In one embodiment, each unit of the charged polymer is charged at the pH present within the nanopore device. In another embodiment, the charged polymer includes a sufficient number of charged units for the polymer to be pulled into and through the pores by electrostatic forces. For example, a charged polymer for purposes of this invention may include a peptide containing a sufficient number of entities that are charged at a selected pH (lysine, aspartic acid, glutamic acid, etc.) so as to be used in the devices and methods described herein. Likewise, a charged polymer for purposes of this invention may include a copolymer comprising methacrylic acid and ethylene if there is a sufficient number of charged carboxylate groups of the methacrylic acid residue to be used in the devices and methods described herein. In one embodiment, the charged polymer is comprised of one or more charged units at or close to one terminus of the polymer. In another embodiment, the charged polymer is comprised of one or more charged units at or close to both termini of the polymer. One co-polymer example is DNA wrapped around protein (e.g. DNA/nucleosome). Another example of a co-polymer is linearized protein conjugated to DNA at the N- and C-terminus.

In one embodiment the solution is responsible for the addition of charge. This could be accomplished, for example, by performing the method at a particular pH to introduce charge to molecules in the test solution. This can also be accomplished by adding components to the testing solution. For example, the addition of sodium dodecyl sulfate adds a uniform negative charge to denatured protein, which would allow it to translocate through the pore when a voltage differential is applied.

Association Sites

When nucleic acids and/or polypeptides form the polymer scaffold, an association site can be a nucleotide or peptide sequence that is recognizable by a target molecule, which is typically a portion of a protein. For nucleic acid binding sites, for instance, there are proteins that specifically recognize and bind to specific sequence motifs, such as promoters and enhancers, or modified DNA, such as modified cytosines (mCpG, fCpG, hcCpG, caCpG) or thymine-thymine dimers, or biotin modifications, or that bind to certain secondary structures such as a bent structure (step loop or hair pin) or to sequences with single-strand breakage.

In some aspects, the association site includes a chemical modification that causes or facilitates recognition and binding by a binding domain. For example, avidin family members can bind to biotin added to, or incorporated into, the polymer scaffold. As another example, methylated DNA sequences can be recognized by transcription factors, DNA methyltransferases or methylation repair enzymes.

Target Molecules

In the present technology, a target molecule is detected or quantitated by virtue of its association to a polymer scaffold.

Examples of target molecules include, without limitation, a peptide, a nucleic acid, a stretch of nucleic acids (double stranded or single stranded), an antigen, an antibody (or antibody fragment), a hormone, a neurotransmitter, a cytokine, a metabolite, a vitamin, a sugar/saccharide, a growth factor, a cell recognition molecule/receptor, an ion, an element, a chelate agent, an ion binding protein such as a calmodulin, a gene regulatory transcription factor, a hormone-dependent DNA binding protein, and any other suitable protein.

Measurement of Affinity of Binding

The present technology can be used also for measuring the binding affinity of the target to the association site. In this case, the association site is a binding site. For instance, after the association site passes through the pore of a nanopore device, the device can be reconfigured to reverse the movement direction of the polymer scaffold (as described below) such that the association site can pass through the pore again.

Prior to the association site entering the pore again, one can change the conditions in the sample that is loaded into the nanopore device. For instance, changing the condition can be one or more of removing the target molecule from the sample, adding a molecule that competes with the target molecule or the ligand for binding, and changing the pH, salt concentration, or temperature. Additionally or alternatively, a duration of time can be the variable and changing the condition may include waiting a duration of time before again performing the detection methods.

Under the changed conditions, the association site may be passed through the pore again. It can then be detected whether the target molecule is still bound to the fusion molecule, therefore determining how the changed conditions impact the binding.

In some aspects, once the association site is in the pore, it is retained there while the conditions are changed, and thus the impact of the changed conditions can be measured in situ.

Alternatively or in addition, the polymer scaffold can include multiple association sites and each of the association sites can bind to a target molecule. While each association site passes through the pore, the conditions of the sample can be changed, allowing detection of changed binding between the target molecule and its association site on a continued basis.

Multiplexing

In some aspects, rather than including multiple association sites of the same kind, as described above, a polymer scaffold can include multiple types of association sites, each type of association site configured to bind to a different target molecule.

Figure 2:
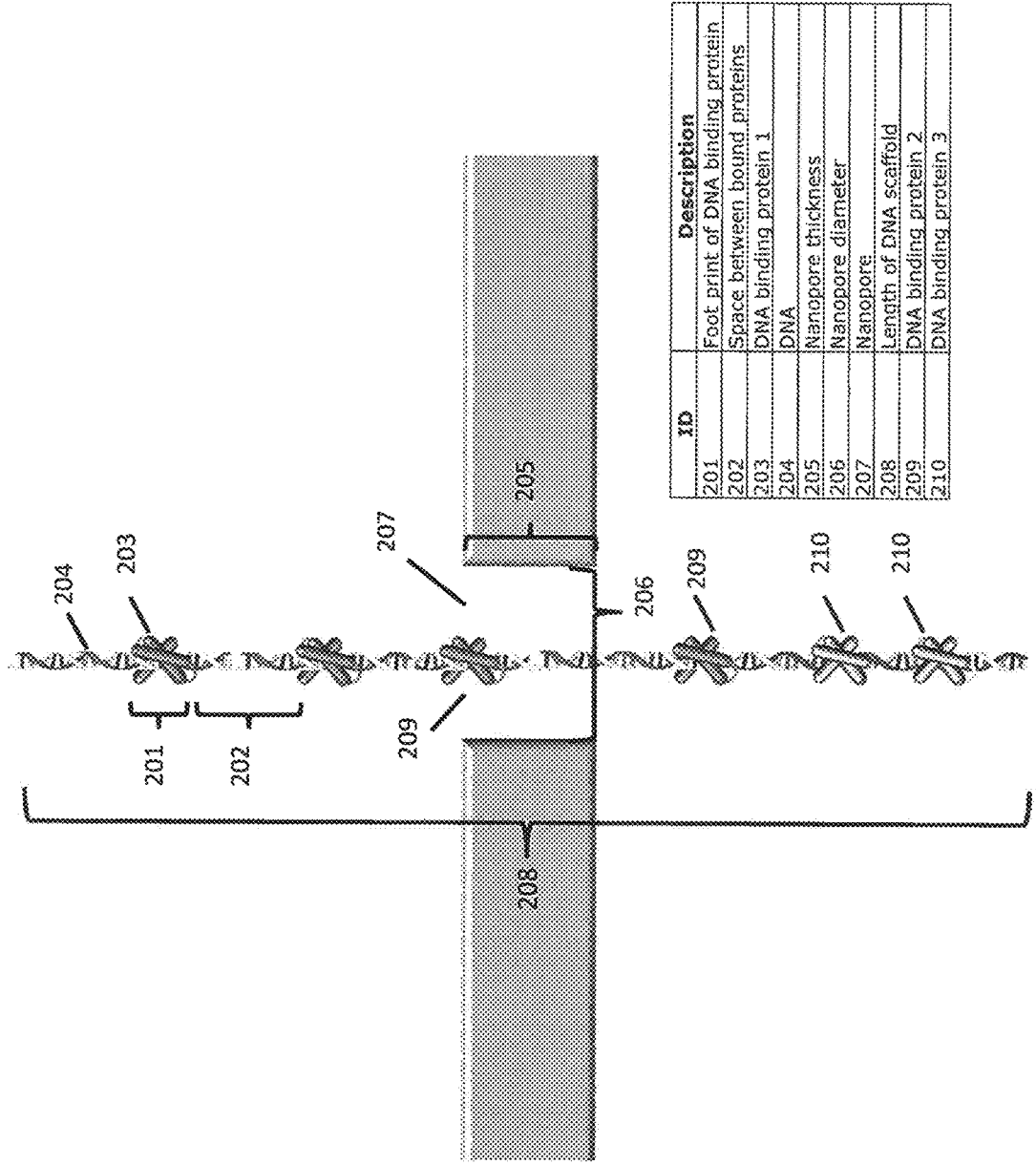
FIG. 2 provides an illustration of another embodiment of a nanopore device with a polymer scaffold extending through a pore of the device. In the depicted embodiment, a double-stranded DNA is used as the polymer scaffold and three different DNA binding proteins are attached, and in a disclosed method, detected. In the depicted embodiment, each DNA binding protein binds at two sites of association on the scaffold.

With such a setting, a single polymer scaffold can be used to detect multiple types of target molecules. FIG. 2 illustrates such a system and method. Here, a double-stranded DNA 204 is used as the polymer scaffold, and the dsDNA includes multiple association sites, for example, two copies of a first type of association sites 203, two copies of a second type of association sites 209, and two copies of a third type of association sites 210.

This way, with a single polymer and single nanopore device, the present technology can simultaneously detect multiple different target molecules. Further, by determining how many copies of association sites are bound to a target molecule, and by tuning conditions that impact the bindings, the system can obtain more detailed binding dynamic information.

An additional method of multiplexing includes assaying a collection of different scaffold molecules during a test, with each different scaffold associating with different target molecule(s). To determine what target molecules are in solution, scaffolds of the same type are labeled such that the sensor can identify what target molecule will bind to that particular scaffold. This can be accomplished, for example, by bar coding each type of scaffold with polyethylene glycol molecules of varying lengths or sizes.

Nanopore Devices

A nanopore device, as provided, includes at least a pore that forms an opening in a structure separating an interior space of the device into two volumes, and at least a sensor configured to identify objects passing through the pore.

In some embodiments, the pore is a protein channel inserted in a lipid bilayer. In other embodiments, the pore is a passageway extending through a synthetic membrane or substrate. In some embodiments, the pore is engineered by drilling, etching, using a voltage-pulse method, or otherwise forming a hole through a solid-state substrate, such as silicon nitride, silicon dioxide, grapheme, or layers of combinations of these or other materials. In at least some embodiments, the pore has a diameter no smaller than 0.1 nm and no larger than 1 micron. The length/depth of the pore may be governed by the thickness of the membrane or substrate and may be, for example, as small as 0.1 nm or as larger as 1 micron or larger. For pores having a length/depth greater than a few hundred nanometers, the term "nanochannel" or "channel" may also be used to describe the pore.

The nanopore device of various embodiments combines the pore with a sensor for sensing objects passing through the pore. In at least some embodiments, sensing or identifying objects passing through the pore comprises detecting changes in measurable parameters, which are indicative of objects passing through the pore.

The pore(s) in the nanopore device are of a nano scale. In one aspect, each pore has a size that allows a small or large molecule to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

The nanopore device can further include means to move a polymer scaffold across the pore and/or means to identify objects that pass through the pore. In a preferred embodiment, a pair of electrodes acts as both the sensing means and the voltage-generation means; in such embodiments, the sensor of the nanopore device comprises the electrodes. Further details are provided below, described in the context of a two-pore device. Compared to a single-pore nanopore device, a two-pore device can be more easily configured to provide good control of speed and direction of the polymer moving across the pores.

In one embodiment, the nanopore device includes a plurality of chambers, each chamber in communication with an adjacent chamber through at least one pore. Among these pores, two pores, namely a first pore and a second pore, are placed to allow at least a portion of a polymer to move out of the first pore and into the second pore. Further, the device includes a sensor capable of identifying the polymer during movement. In one aspect, the identification entails identifying individual components of the polymer. In another aspect, the identification entails identifying target molecules bound to the polymer. When a single sensor is employed, the single sensor may include two electrodes placed at both ends of a pore to measure an ionic current across the pore. In another embodiment, the single sensor comprises a component other than electrodes.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymers to move from one chamber to the next simultaneously. Such a multi-pore design can enhance throughput of polymer analysis in the device.

In some aspects, the device further includes means to enable movement of a polymer from one chamber to another. In one aspect, the movements result in extending the polymer across both the first pore and the second pore at the same time. In another aspect, the movement means further enables the movement of the polymer, through both pores, at the same direction. In some embodiments, the movement means includes electrodes coupled to a power supply. In some embodiments, a sensitive voltage-clamp amplifier is used to apply a voltage across the pore while measuring current through the pore. In some such embodiments, when a single charged molecule is captured and driven through the pore by electrophoresis, the measured current shifts, and the duration and amount (i.e., amplitude) of the shift are used to characterize the event. The event or a distribution of a plurality of events may be analyzed to characterize the sample according to the target molecules contained therein. In this way, the nanopore device described herein provides a simple, label-free, purely electrical method of sensing single molecules.

In one example, in a three-chamber two-pore device (a "two-pore" device), each of the chambers can contain an electrode for connecting to a power supply so that a separate voltage can be established across each of the pores between the chambers. In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore. Such a device may have any of the dimensions or other characteristics previously disclosed in U.S. Publ. No. 2013-0233709, entitled Dual-Pore Device, which is herein incorporated by reference in its entirety.

Figure 5A:
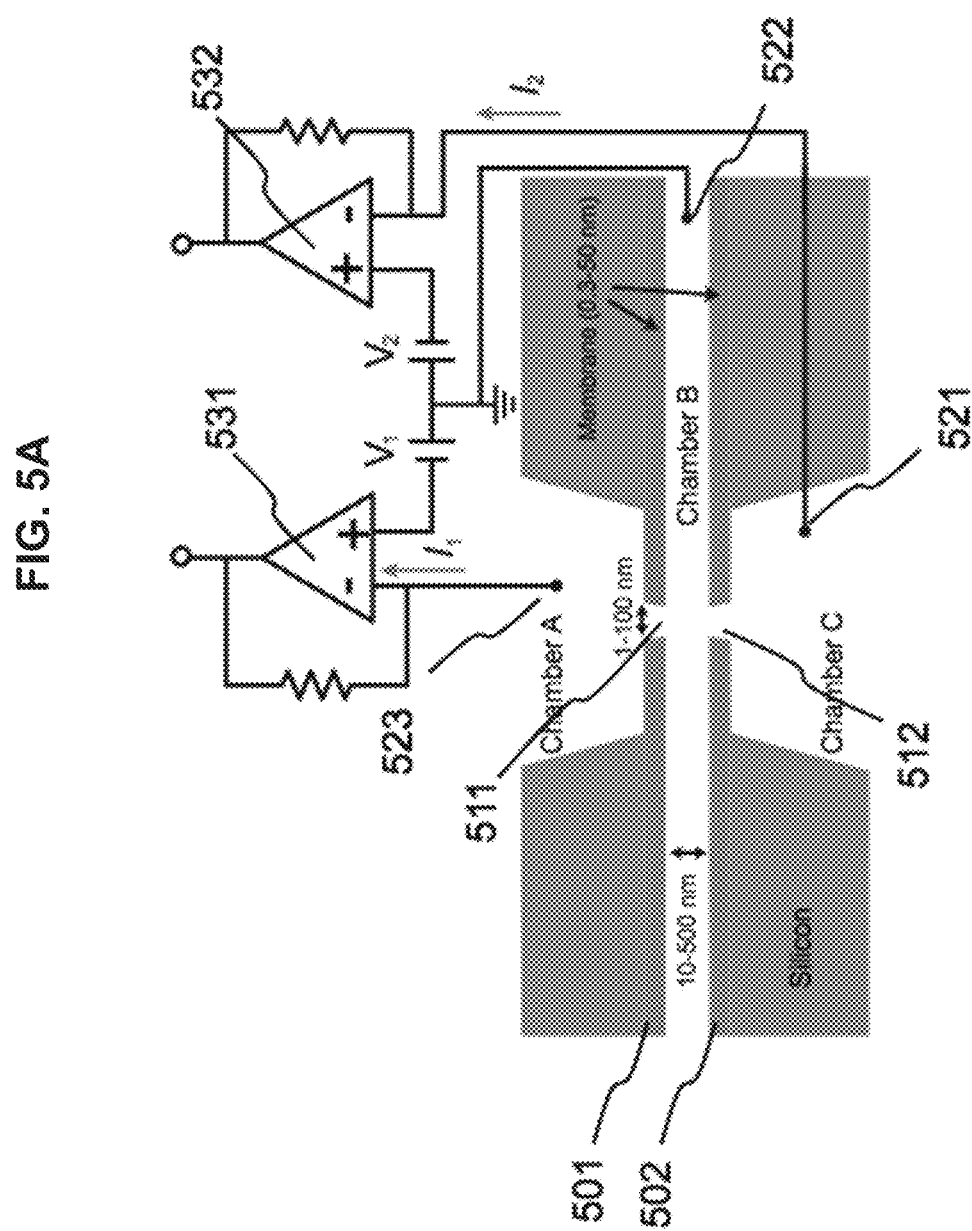
FIGS. 5A-5C illustrate various embodiments of a nanopore device with at least two pores separating multiple chambers.

With reference to FIG. 5A, the device includes an upper chamber (Chamber A), a middle chamber (Chamber B), and a lower chamber (Chamber C). The chambers are separated by two separating layers or membranes (501 and 502) each having a separate pore (511 and 512). Further, each chamber contains an electrode (521, 522 and 523) for connecting to a power supply. It is apparent that the annotation of upper, middle and lower chamber is in relative terms and does not indicate that, for instance, the upper chamber is placed above the middle or lower chamber relative to the ground, or vice versa.

Each of the pores (511 and 512) independently has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm in diameter.

In some aspects, the pore(s) in the nanopore device are of a larger scale for detecting large microorganisms or cells. In one aspect, each pore has a size that allows a large cell or microorganism to pass. In one aspect, each pore is at least about 100 nm in diameter. Alternatively, each pore is at least about 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, or 5000 nm in diameter.

In one aspect, the pore is no more than about 10000 nm in diameter. Alternatively, the pore is no more than about 9500 nm, 9000 nm, 8500 nm, 8000 nm, 7500 nm, 7000 nm, 6500 nm, 6000 nm, 5500 nm, 5000 nm, 4500 nm, 4000 nm, 3500 nm, 3000 nm, 2500 nm, 2000 nm, 1500 nm, or 1000 nm in diameter.

In one aspect, the pore has a diameter that is between about 100 nm and about 10000 nm, or alternatively between about 200 nm and about 9000 nm, or between about 300 nm and about 8000 nm, or between about 400 nm and about 7000 nm, or between about 500 nm and about 6000 nm, or between about 1000 nm and about 5000 nm, or between about 1500 nm and about 3000 nm.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore has a substantially round shape. "Substantially round", as used here, refers to a shape that is at least about 80 or 90% in the form of a cylinder. In some embodiments, the pore is square, rectangular, triangular, oval, or hexagonal in shape.

Each of the pores (511 and 512) independently has a depth (i.e., a length of the pore extending between two adjacent volumes). In one aspect, each pore has a depth that is least about 0.3 nm. Alternatively, each pore has a depth that is at least about 0.6 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm.

In one aspect, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm.

In one aspect, the pore has a depth that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the length or depth of the nanopore is sufficiently large so as to form a channel connecting two otherwise separate volumes. In some such aspects, the depth of each pore is greater than 100 nm, 200 nm, 300 nm, 400 nm, 500 nm, 600 nm, 700 nm, 800 nm, or 900 nm. In some aspects, the depth of each pore is no more than 2000 nm or 1000 nm.

In one aspect, the pores are spaced apart at a distance that is between about 10 nm and about 1000 nm. In some aspects, the distance between the pores is greater than 1000 nm, 2000 nm, 3000 nm, 4000 nm, 5000 nm, 6000 nm, 7000 nm, 8000 nm, or 9000 nm. In some aspects, the pores are spaced no more than 30000 nm, 20000 nm, or 10000 nm apart. In one aspect, the distance is at least about 10 nm, or alternatively at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm. In yet another aspect, the distance is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no blockage directly between them. Still, in one aspect, the pores are substantially coaxial, as illustrated in FIG. 5A.

In one aspect, the device, through the electrodes in the chambers, is connected to one or more power supply. In some aspects, the power supply is comprised of a voltage-clamp or a patch-clamp, which can supply a voltage across each pore and measure the current through each pore independently. In this respect, the power supply can set the middle chamber to a common ground for both voltage sources. In one aspect, the power supply is configured to provide a first voltage between the upper chamber (e.g., Chamber A in FIG. 5A) and the middle chamber (e.g., Chamber B in FIG. 5A), and a second voltage between the middle chamber and the lower chamber (e.g., Chamber C in FIG. 5A).

In some aspects, the first voltage and the second voltage are independently adjustable. In one aspect, the middle chamber is adjusted to be ground relative to the two voltages. In one aspect, the middle chamber comprises a medium for providing conductance between each of the pores and the electrode in the middle chamber. In one aspect, the middle chamber comprises a medium for providing a resistance between each of the pores and the electrode in the middle chamber. Keeping such a resistance sufficiently small, relative to the nanopore resistances, is useful for decoupling the two voltages and currents across the pores, which is helpful for the independent adjustment of the voltages.

Adjustment of the voltages can be used to control the movement of charged particles in the chambers. For instance, when both voltages are set in the same direction, a properly charged particle can be moved from the upper chamber to the middle chamber and to the lower chamber, or the other way around, sequentially. Otherwise, a charged particle can be moved from either the upper or the lower chamber to the middle chamber and kept there.

The adjustment of the voltages in the device can be particularly useful for controlling the movement of a large molecule, such as a charged polymer, that is long enough to cross both of the pores at the same time. In such an aspect, the movement and the rate of movement of the molecule can be controlled by the relative magnitude and direction of the voltages, which will be further described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. A single sheet of graphene forms a membrane about 0.3 nm thick, and can be used as the pore-bearing membrane, for example.

Figure 5B:
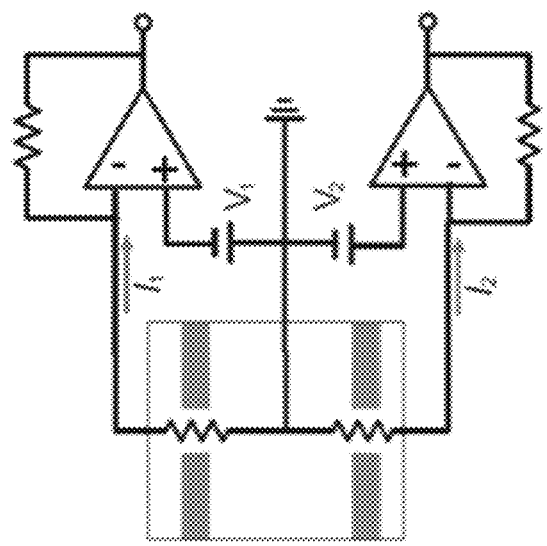

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C. In one aspect, the housing would provide minimal access resistance between the voltage electrodes (two sources and one ground) and the nanopores, to ensure that each voltage is applied principally across each pore (see, e.g., FIG. 5B).

In one aspect, the device contains a microfluidic chip (labeled as "Dual-pore chip") comprised of two parallel membranes connected by spacers. Each membrane contains a pore (not shown) drilled by a single beam through the center of the membrane. Further, the device preferably has a Teflon® housing for the chip. The housing ensures sealed separation of Chambers A-C (FIG. 5A) and provides minimal access resistance for the electrolyte to ensure that each voltage is applied principally across each pore.

More specifically, the pore-bearing membranes can be made with TEM (transmission electron microscopy) grids with 5-100 nm thick silicon, silicon nitride, or silicon dioxide windows. Spacers can be used to separate the membranes, using an insulator (such as, for example, SU-8, photoresist, PECVD oxide, ALO oxide, or ALO alumina) or an evaporated metal (e.g., Ag, Au, Pt) material, and occupying a small volume within the otherwise aqueous portion of Chamber B between the membranes. A holder is seated in an aqueous bath that comprises the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying the correct beam focus to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

In another aspect, insertion of biological nanopores into solid-state nanopores to form a hybrid pore can be used in either or both nanopores in the two-pore method (Hall et al., *Nat. Nanotech.*, 5(12):874-7, 2010). The biological pore can increase the sensitivity of the ionic current measurements, and is useful when only single-stranded polynucleotides are to be captured and controlled in the two-pore device, e.g., for sequencing.

By virtue of the voltages present at the pores of the device, charged molecules can be moved through the pores between chambers. Speed and direction of the movement can be controlled by the magnitude and direction of the voltages. Further, because each of the two voltages can be independently adjusted, the movement and speed of a charged molecule can be finely controlled in each chamber.

One example concerns a charged polymer scaffold, such as a DNA, having a length that is longer than the combined distance that includes the depth of both pores plus the distance between the two pores. For example, a 1000 bp dsDNA is about 340 nm in length, and would be substantially longer than the 40 nm spanned by two 10 nm-length pores separated by 20 nm. In a first step, the polynucleotide is loaded into either the upper or the lower chamber. By virtue of its negative charge under a physiological condition (at a pH of about 7.4), the polynucleotide can be moved across a pore on which a voltage is applied. Therefore, in a second step, two voltages, in the same direction and at the same or similar magnitudes, are applied to the pores to induce movement of the polynucleotide across both pores sequentially.

Figure 5C:
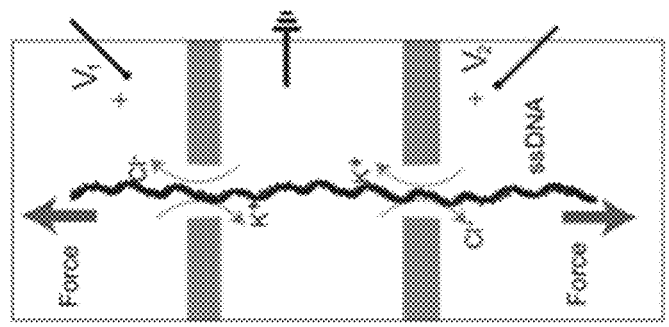

At about the time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of direction (i.e., polarity) of the voltage at the first pore, therefore, will generate a force that pulls the polynucleotide away from the second pore as illustrated in FIG. 5C.

Assuming that the two pores have identical voltage-force influence and $|V_1|=|V_2|+\delta V$, the value $\delta V>0$ (or <0) can be adjusted for tunable motion in the $V_1$ (or $V_2$) direction. In practice, although the voltage-induced force at each pore will not be identical with $V_1=V_2$, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications.

Accordingly, in one aspect, provided is a method for controlling the movement of a charged polymer through a nanopore device. The method entails (a) loading a sample comprising a charged polymer in one of the upper chamber, middle chamber or lower chamber of the device of any of the above embodiments, wherein the device is connected to one or more power supplies for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber (voltage-competition mode), wherein the two voltages are different in magnitude, under controlled conditions, so that the charged polymer moves across both pores in either direction and in a controlled manner. In some embodiments, an environmental gradient, such as a temperature gradient or concentration gradient may be used in parallel with the voltage to help drive the scaffold of interest across a pore.

To establish the voltage-competition mode in step (c), the relative force exerted by each voltage at each pore is to be determined for each two-pore device used, and this can be done with calibration experiments by observing the influence of different voltage values on the motion of the polynucleotide, which can be measured by sensing known-location and detectable features in the polynucleotide, with examples of such features detailed later in this disclosure. If the forces are equivalent at each common voltage, for example, then using the same voltage value at each pore (with common polarity in upper and lower chambers relative to the grounded middle chamber) creates a zero net motion in the absence of thermal agitation (the presence and influence of Brownian motion is discussed below). If the forces are not equivalent at each common voltage, achieving equal forces involves the identification and use of a larger voltage at the pore that experiences a weaker force at the common voltage. Calibration for voltage-competition mode can be done for each two-pore device and for specific charged polymers or molecules whose features influence the force when passing through each pore.

In one aspect, the sample containing the charged polymer is loaded into the upper chamber and the initial first voltage is set to pull the charged polymer from the upper chamber to the middle chamber and the initial second voltage is set to pull the polymer from the middle chamber to the lower chamber. Likewise, the sample can be initially loaded into the lower chamber, and the charged polymer can be pulled to the middle and the upper chambers.

In another aspect, the sample containing the charged polymer is loaded into the middle chamber and the initial first voltage is set to pull the charged polymer from the middle chamber to the upper chamber and the initial second voltage is set to pull the charged polymer from the middle chamber to the lower chamber.

In one aspect, the adjusted first voltage and second voltage at step (c) are about 10 times to about 10,000 times as high, in magnitude, as the difference/differential between the two voltages. For instance, the two voltages are 90 mV and 100 mV, respectively. The magnitude of the voltages (~100 mV) is about 10 times of the difference/differential between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference/differential between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference/differential between them.

In one aspect, real-time or on-line adjustments to first voltage and second voltage at step (c) are performed by active control or feedback control using dedicated hardware and software at clock rates up to hundreds of megahertz. Automated control of the first or second or both voltages is based on feedback of the first or second or both ionic current measurements.

Sensors

The nanopore device further includes one or more sensors to carry out the identification of the association status of the association sites.

The sensors used in the device can be any sensor suitable for identifying a molecule or particle, such as a polymer. For instance, a sensor can be configured to identify the polymer by measuring a current, a voltage, a pH value, an optical feature or residence time associated with the polymer. In other aspects, the sensor may be configured to identify one or more individual components of the polymer or one or more components bound to the polymer. The sensor may be formed of any component configured to detect a change in a measurable parameter where the change is indicative of the polymer, a component of the polymer, or preferably, a component bound to the polymer passing through the pore. In one aspect, the sensor includes a pair of electrodes placed at two sides of a pore to measure an ionic current across the pore when a molecule or particle, in particular a polymer, moves through the pore.

In certain aspects, the ionic current across the pore changes measurably when an association site of the polymer passing through the pore is bound to a target molecule. Such changes in current may vary in predictable, measurable ways corresponding with, for example, the presence, absence, and/or size of the target molecules present. In some multiplexing embodiments, where one scaffold having a plurality of structurally different association sites is used to detect the presence or absence of a plurality of different target molecules, the presence of the various target molecules is distinguishable based on the size of the target molecules and the resulting change in current amplitude. In other multiplexing embodiments, the presence of the various target molecules is distinguishable based on the timing of the changes in current and the known location of each target molecule's corresponding association site along the polymer scaffold.

In one embodiment, the sensor measures an optical feature of the polymer, a component (or unit) of the polymer, or preferably, a target bound to the polymer. One example of such measurement includes identification of an absorption band unique to a particular target by infrared (or ultraviolet) spectroscopy.

When residence time measurements are used, the presence of the target on the scaffold can be determined by measuring the length of time the scaffold takes to pass through the sensing device. A change in the translocation time will correlate with bound versus unbound scaffold.

In some embodiments, the sensor is functionalized with reagents that form distinct non-covalent bonds with each association site or each associated target molecule. In this respect, the gap is large enough to allow effective measuring. For instance, when a sensor is functionalized with reagents to detect a target that is 5 nm on a dsDNA scaffold, a 7.5 nm gap can be used as DNA is 2.5 nm.

Tunnel sensing with a functionalized sensor is termed "recognition tunneling." Using current technology, a Scanning Tunneling Microscope (STM) with recognition tunneling identifies a DNA base flanked by other bases in a short DNA oligomer. As been described, recognition tunneling can provide a "universal reader" designed to hydrogen-bond in a unique orientation to molecules that a user desires to be detected. Most reported is the identification of nucleic acids; however, it is herein modified to be employed to detect target molecules on a scaffold.

A limitation with the conventional recognition tunneling is that it can detect only freely diffusing molecules that randomly bind in the gap, or that happen to be in the gap during microscope motion, with no method of explicit capture in the gap. However, the collective drawbacks of the STM setup can be eliminated by incorporating the recognition reagent, optimized for sensitivity, within an electrode tunneling gap in a nanopore channel.

Accordingly, in one embodiment, the sensor comprises surface modification by a reagent. In one aspect, the reagent is capable of forming a non-covalent bond with an association site or an attached target molecule. In a particular aspect, the bond is a hydrogen bond. Non-limiting examples of the reagent include 4-mercaptobenzamide and 1-H-Imidazole-2-carboxamide.

Furthermore, the methods of the present technology can provide DNA delivery rate control for one or more recognition tunneling sites, each positioned in one or both of the nanopore channels, and voltage control can ensure that each target molecule resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can detect target molecules bound to the translocating scaffold.

In some embodiments, the tunnel gap has a width that is from about 1 nm to about 100 nm. In one aspect, the width of the gap is at least about 1 nm, or alternatively at least about 1.5, 2, 2.5, 3, 3.5, 4, 4.5, 5, 6, 7, 8, 9, 10, 12, 15, 20, 30, 40, 50, 60, 70, 80, or 90 nm. In another aspect, the width of the gap is not greater than about 20 nm, or alternatively not greater than about 19, 18, 17, 16, 15, 14, 13, 12, 11, 10, 9, 8, 7, 6, 5, 4, 3, or 2 nm. In another aspect, the width of the gap is not greater than about 100, 95, 90, 85, 75, 70, 65, 60, 55, 50, 45, 40, 35, 30, or 25 nm. In some aspects, the width is between about 1 nm and about 100 nm, between about 10 nm and 50 nm, between about 1 nm and about 15 nm, between about 1 nm and about 10 nm, between about 2 nm and about 10 nm, between about 2.5 nm and about 10 nm, or between about 2.5 nm and about 5 nm.

In some embodiments, the sensor is an electric sensor. In some embodiments, the sensor detects a fluorescent detection means when the target molecule or the detectable label passing through has a unique fluorescent signature. A radiation source at the outlet can be used to detect that signature.

EXAMPLES

The present technology is further defined by reference to the following examples and experiments. It will be apparent to those skilled in the art that many modifications may be practiced without departing from the scope of the current invention.

Example 1—DNA Alone in Solid-State Nanopore Experiment

Figure 4C:
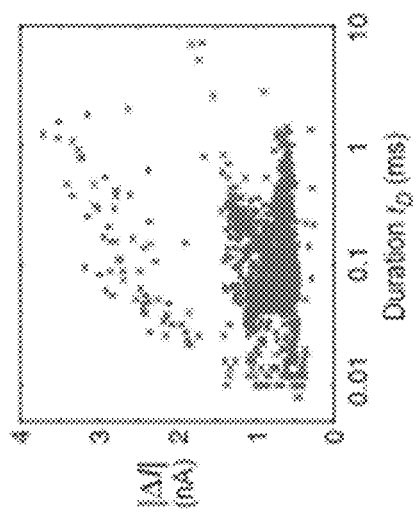
FIGS. 4A-4C illustrate a nanopore device and potential results from a method of using said device.
Figure 4B:
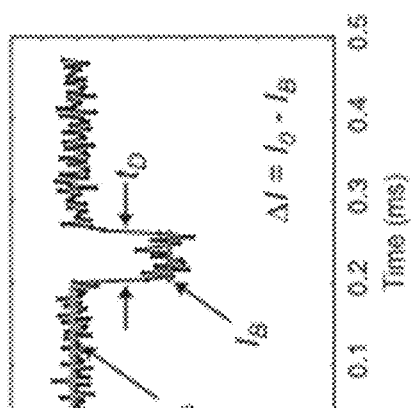
Figure 4A:
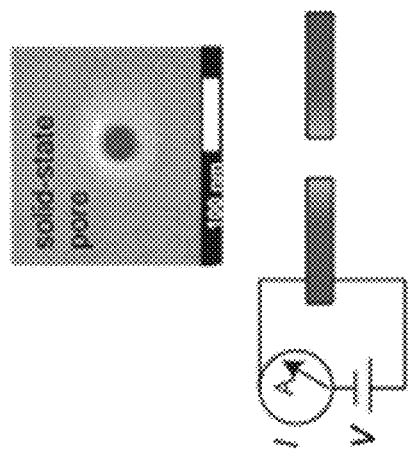

Nanopore instruments use a sensitive voltage-clamp amplifier to apply a voltage V across the pore while measuring the ionic current $l_0$ through the open pore (FIG. 4A). When a single charged molecule such as a double-stranded DNA (dsDNA) is captured and driven through the pore by electrophoresis (FIG. 4B), the measured current shifts from $l_0$ to $l_B$, and the shift amount $\Delta l = l_0 - l_B$ and duration $t_D$ are used to characterize the event. After recording many events during an experiment, distributions of the events (FIG. 4C) may be analyzed to characterize the corresponding molecule. In this way, nanopores provide a simple, label-free, purely electrical single-molecule method for biomolecular sensing.

In the DNA experiment shown in FIGS. 4A-4C, the single nanopore fabricated in silicon nitride (SiN) substrate is a 40 nm diameter pore in a 100 nm thick SiN membrane (FIG. 4A). In FIG. 4B, the representative current trace shows a blockade event caused by a 5.6 kb dsDNA passing in a single file manner (unfolded) through an 11 nm diameter nanopore in 10 nm thick SiN at 200 mV and 1M KCl. The mean open channel current is $l_0 = 9.6$ nA, with mean event amplitude $l_B = 9.1$ nA, and duration $t_D = 0.064$ ms. The amplitude shift is $\Delta l = l_0 - l_B = 0.5$ nA. In FIG. 4C, the scatter plot shows $|\Delta l|$ vs. $t_D$ for all 1301 events recorded over 16 minutes.

Figure 6A:
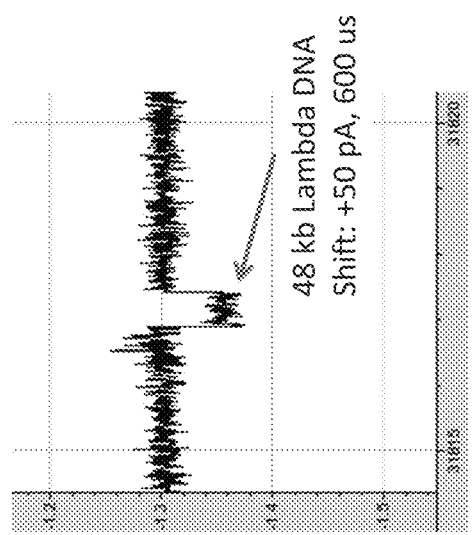
FIGS. 6A and 6B depict additional examples of current profiles detected using an embodiment of the nanopore device disclosed herein. The figures show that dsDNA alone causes current enhancement events at KCl concentrations below 0.4 M. Current enhancements are downward shifts in this experiment, since the voltage and current are both negative. Specifically, in DNA-alone control experiments using a 10-11 nm diameter pore in 0.1M KCl at −200 mV, a 5.6 kb dsDNA scaffold causes brief current enhancement events that are 50-70 pA in amplitude and 10-200 microseconds in duration. (See FIG. 6A.) Likewise, 48 kb Lambda DNA causes current enhancement events 50-70 pA in amplitude and 50-2000 microseconds in duration (See FIG. 6B.)
Figure 6B:
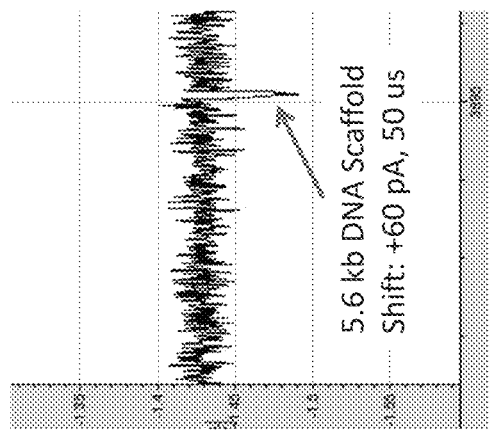

In the DNA experiment shown in FIGS. 6A-6B, dsDNA alone causes current enhancement events at 100 mM KCl. This was shown in the published research Smeets, Ralph M M, et al. "Salt dependence of ion transport and DNA translocation through solid-state nanopores." *Nano Letters* 6.1 (2006): 89-95). The study showed that, while the amplitude shift $\Delta l = l_0 - l_B > 0$ for KCl concentration above 0.4 M, the shift has opposite polarity ($\Delta l < 0$) for KCl concentration below 0.4 M.

Example 2—VspR Protein Binding to DNA Scaffold and Nanopore Detection

Figure 7:
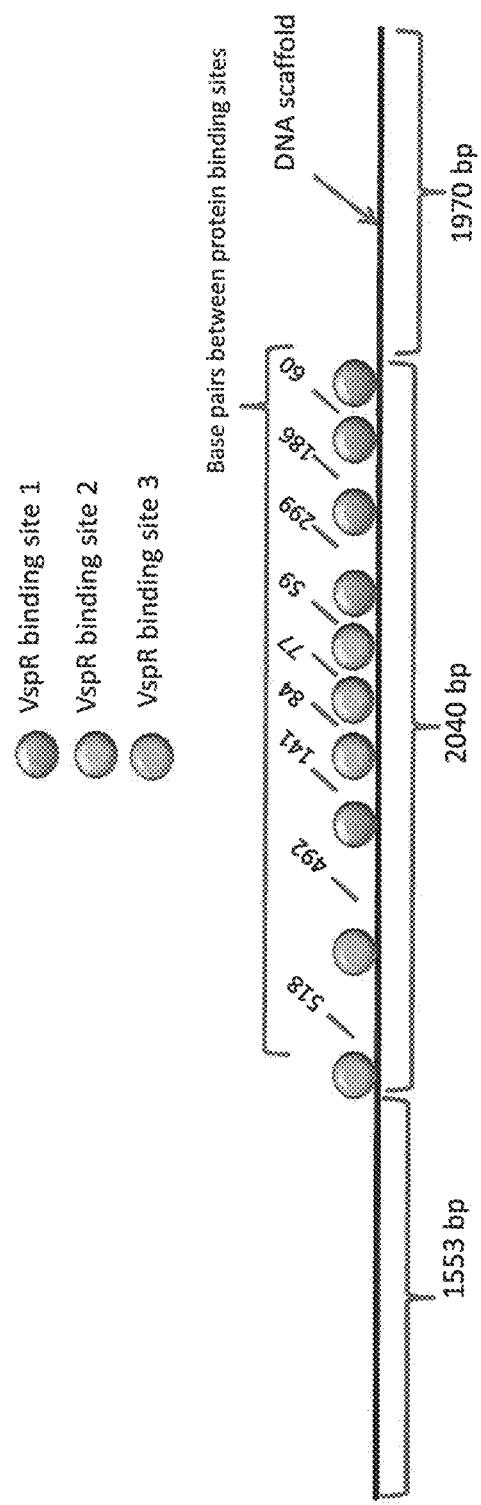
FIG. 7 shows one non-limiting example of a polymer scaffold in accordance with an embodiment of the scaffolds disclosed herein. Specifically.

The VspR protein is a *V. cholerae* biomarker (90 kDa) that binds directly to dsDNA with high micromolar affinity (see reference: Yildiz, Fitnat H., Nadia A. Dolganov, and Gary K. Schoolnik. "VpsR, a Member of the Response Regulators of the Two-Component Regulatory Systems, Is Required for Expression of Biosynthesis Genes and EPSETr-Associated Phenotypes in *Vibrio cholerae* 01 El Tor." *Journal of bacteriology* 183, no. 5 (2001): 1716-1726). In an example conducted in accordance with systems and methods disclosed herein, direct DNA binding detection was performed using nanopore technology, and detection was accomplished via direct binding of VspR proteins to a scaffold that contains 10 VspR specific binding sites (FIG. 7). To preserve affinity of VspR for dsDNA binding, we used 0.1 M KCl, a salt concentration in which DNA-alone translocations cause current enhancements, as shown in Example 1 and FIGS. 6A-6B. The 5.631 kb DNA scaffold contains 10 total VspR binding sites: 5 of one sequence (14 base pairs), 3 of a different sequence (18 base pairs), and 2 of a third sequence (27 bp). The three different sequences may not bind VspR with equal affinity. In experiments, VspR protein concentration is 18 nM in the recording buffer, and 180 nM during labeling (binding step). This results in 18x excess of VspR protein to binding sites on DNA. The experiment was run at pH 8.0 (pI of VspR protein is 5.8). Taking Kd and DNA concentration into account, only 0.1-1% of DNA should be fully occupied by VspR, with a larger percentage partially occupied, and some unknown remaining percentage of DNA entirely unbound. There is also free VspR protein in solution during the nanopore experiment.

Figure 3B:
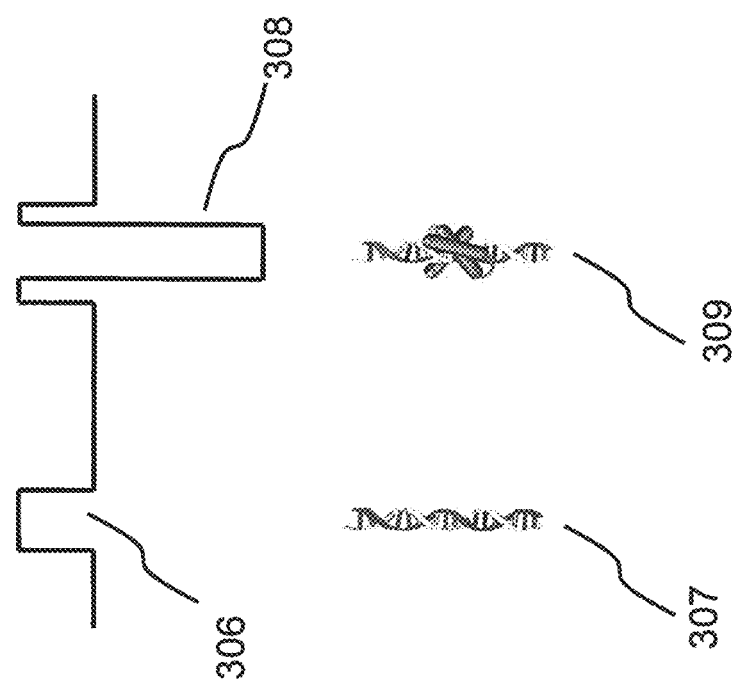
Figure 8:
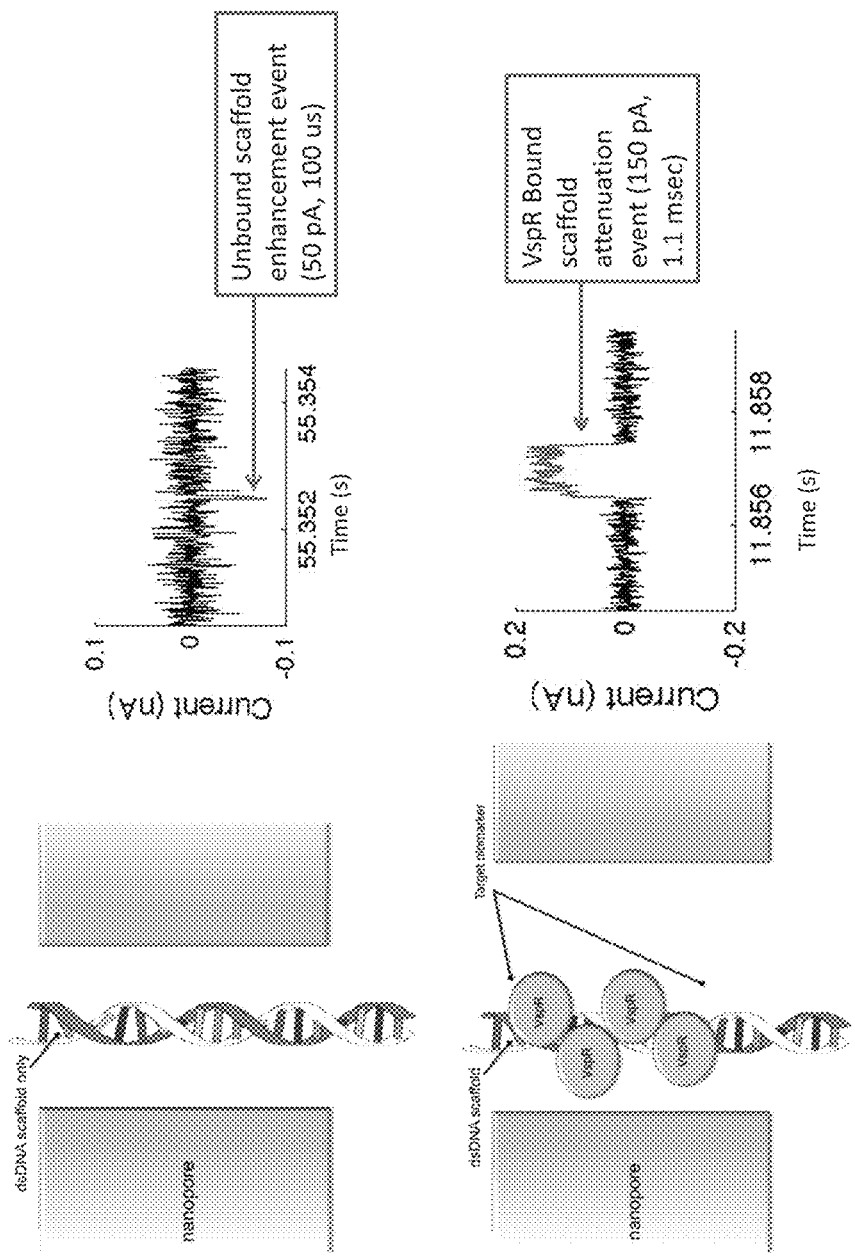
FIGS. 8A and 8B each show schematic representations of embodiments of a nanopore with a scaffold passing therethrough. Each also shows a resultant current profile associated with the scaffold passage as measured by one embodiment of the disclosed nanopore device. In particular, FIGS. 8A and 8B compare events with DNA scaffold alone (FIG. 8A) and VspR-bound DNA (FIG. 8B). Specifically.
Figure 9:
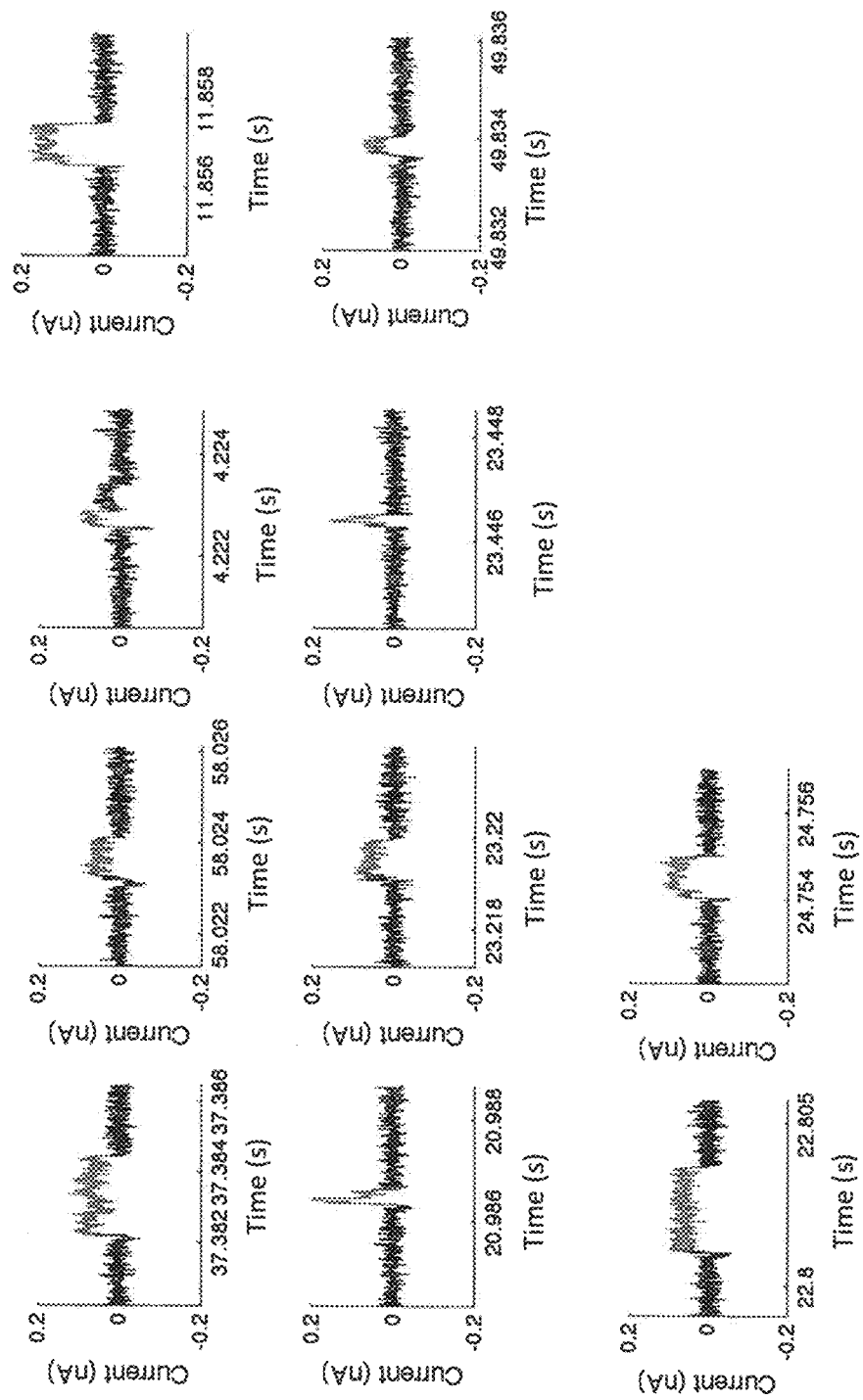
FIG. 9 shows ten more representative current attenuation events depicted in a current profile consistent with the VspR-bound scaffold passing through the pore. All shifts are consistent with current attenuations; the baseline is zeroed for display purposes.

Two representative events are shown in FIGS. 8A and 8B. In the experiments with VspR, VspR concentration was 18 nM (1.6 mg/L), 10 nM binding sites. The scaffold concentration was 1 nM resulting in capture every 6.6 seconds. From this, the theoretical sensitivity using a 10 ul sample is 116 pM (0.01 mg/ml). The pore size is 15 nm in diameter and length. The voltage is −100 mV. Negative voltages create negative currents, so upward shifts correspond to attenuation events, as shown for the VspR-bound DNA event (FIG. 8B), whereas downward shifts create positive shifts as shown for the unbound DNA scaffold event (FIG. 8A). Thus, the key observation from this figure is that VspR-bound events have the opposite signal polarity compared to unbound DNA events. FIG. 9 shows ten more representative current attenuation events consistent with the VspR-bound scaffold passing through the pore. There were 90 such events over 10 minutes of recording, corresponding to 1 VspR-bound event every 6.6 seconds. Events were attenuations of 50 to 150 pA in amplitude and 0.2 to 2 milliseconds in duration. As stated, downward events correspond to current enhancement events and upward events correspond to current attenuation events in FIGS. 8A-8B and FIG. 9, and this shift direction is preserved even though the baseline is zeroed for display purposes. The VspR-bound DNA events show a polarity shift compared to unbound DNA, consistent with the model signal pattern in FIG. 3B; the only difference is that the polarity is reversed, since FIG. 3B presumes a positive voltage.

Example 3—RecA Protein Binding to DNA Scaffold and Nanopore Detection

In this example, RecA serves as a model protein that can be detected when enough RecA molecules are bound to a dsDNA passing through a nanopore. While RecA is not in itself a biomarker, it acts as a model protein demonstrating detection of protein that binds directly to a dsDNA scaffold using nanopore technology. We also discuss and demonstrate the use of an additional probe that can further enhance the nanopore instruments ability to detect RecA-bound DNA molecules as they pass through the nanopore.

Reagent DNA/RecA consists of the 5.6 kb dsDNA scaffold molecule coated in RecA. RecA is a 38 kDa bacterial protein involved in DNA repair, which is capable of polymerizing along dsDNA (see C Bell. Structure and mechanism of *Escherichia coli* RecA ATPase. Molecular microbiology, 58(2):358-366, January 2005). This reagent is created by incubating 60 nM scaffold with 112 uM RecA protein in 10 mM gamma-S-ATP, 70 mM Tris pH 7.6, 10 mM MgCl, and 5 mM OTT (New England Biolabs). Gamma-S-ATP is included since RecA binds to dsDNA with greater affinity if the RecA has ATP bound. Since RecA can hydrolyze ATP to ADP, thereby reducing its affinity for DNA, the non-hydrolyzable gamma-S ATP analog prevents this transition to ADP and thus the higher affinity state is maintained. Even though the ratio of RecA to DNA is one RecA molecule for every possible 3-bp binding site, we expect that not all the RecA protein is binding and thus there is free RecA in solution, as observed in other nanopore studies (see Smeets, R. M. M., S. W. Kowalczyk, A. R. Hall, N. H. Dekker, and C. Dekker. "Translocation of RecAcoated double-stranded DNA through solid-state nanopores." Nano letters 9, no. 9 (2008): 3089-3095, and Kowalczyk, Stefan W., Adam R. Hall, and Gees Dekker. "Detection of local protein structures along DNA using solid-state nanopores." Nano letters 10, no. 1 (2009): 324-328]). DNA/RecA samples are then adjusted to 1M KCl or LiCl, 10 mM EDTA and tested in a nanopore experiment or excess RecA protein is removed using gel filtration (ThermoScientific Spin Columns).

Figure 10:
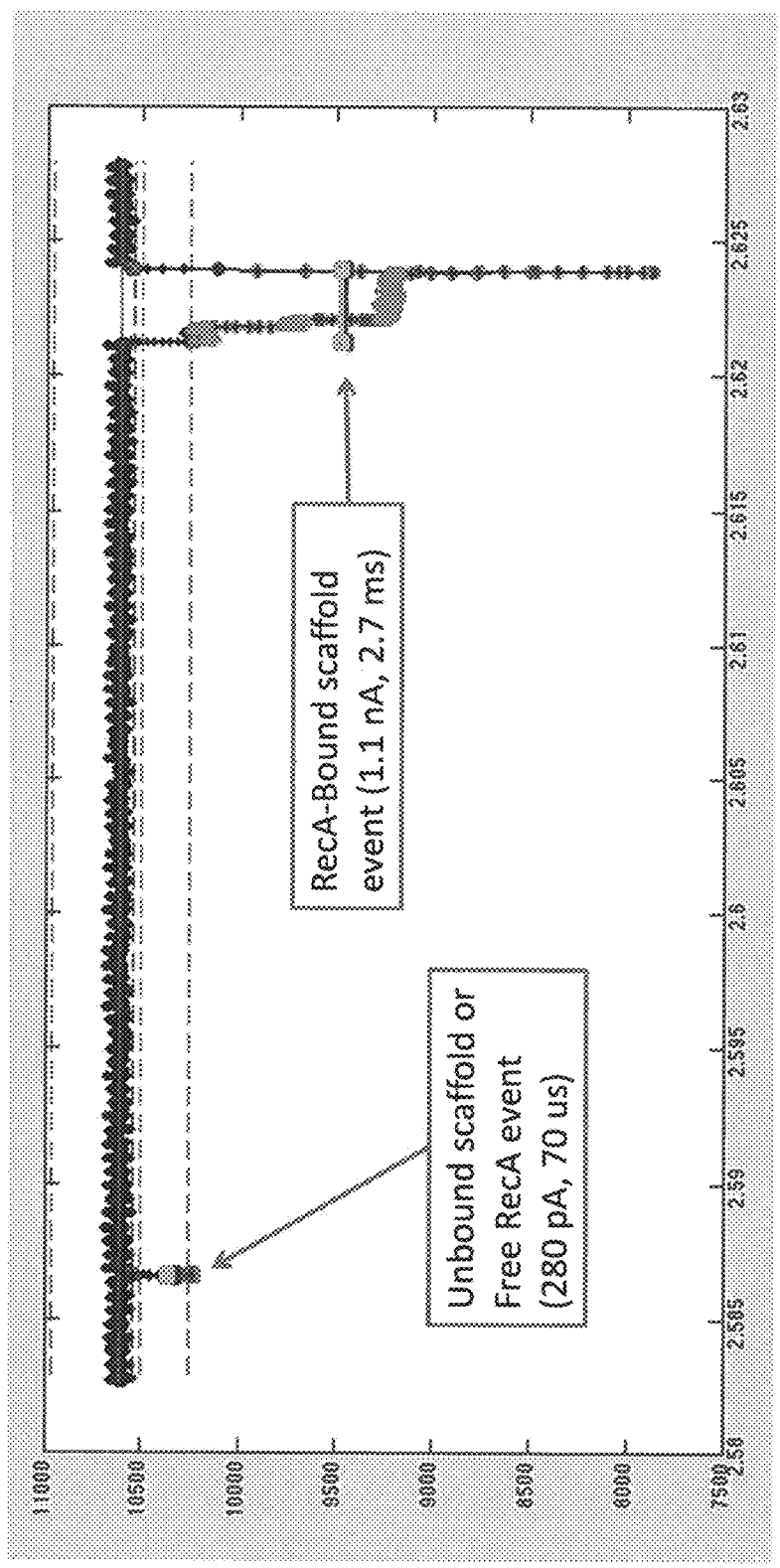
FIG. 10 shows two representative current events depicted in a current profile captured in an experiment with 5.6 kb dsDNA scaffold and RecA protein at 180 mV and 1M KCl using a 16-18 nm diameter nanopore. The first event is consistent with an unbound dsDNA or possibly a free RecA (or multiple associated RecA proteins) passing through the pore, at 280 pA mean current attenuation lasting 70 microseconds. The second event is consistent with RecA-bound scaffold passing through the pore, at 1.1 nA mean current attenuation lasting 2.7 milliseconds. RecA-bound events commonly display deeper blockades with longer duration.
Figure 11:
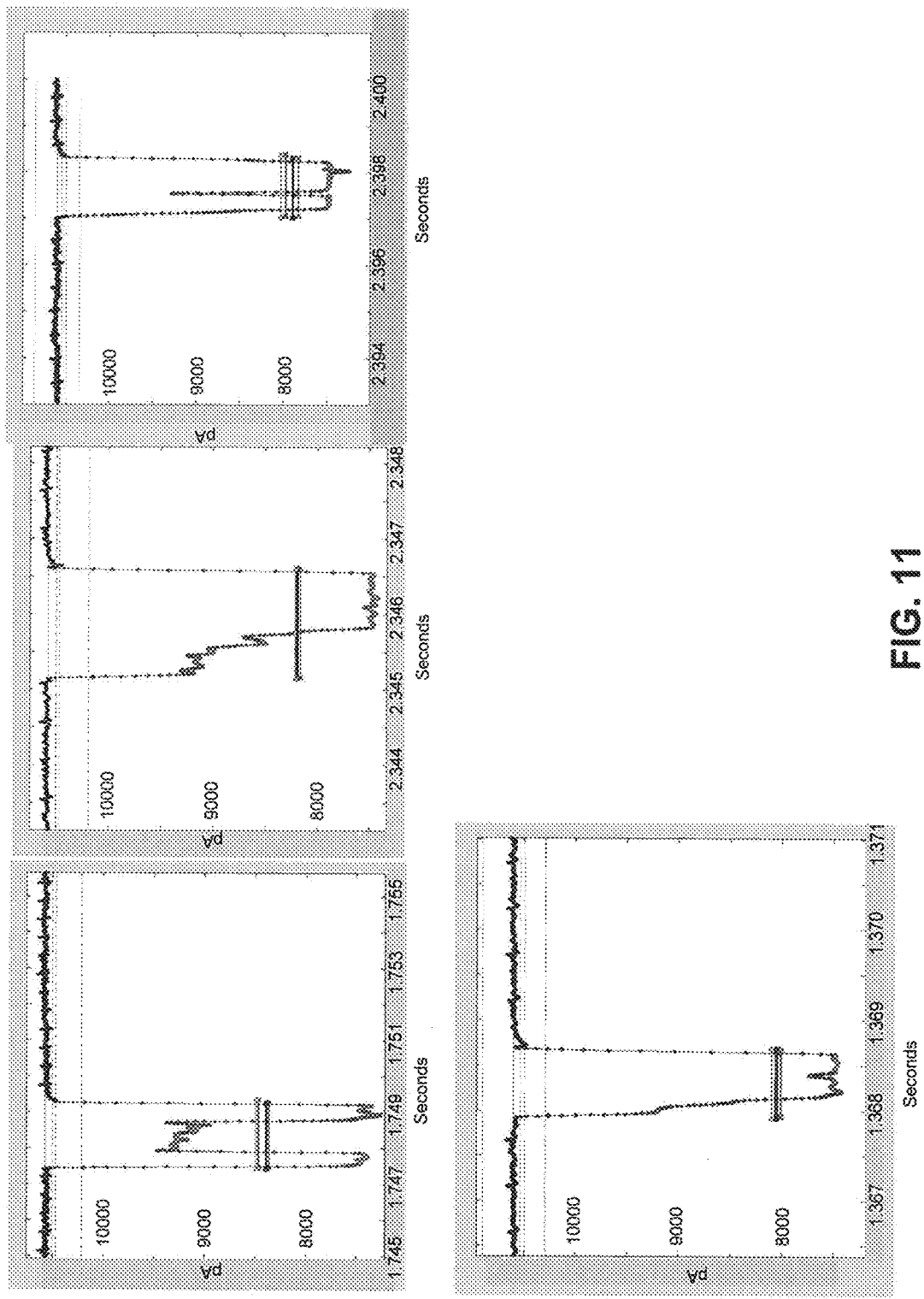
FIG. 11 shows four more representative current events depicted in a current profile consistent with RecA-bound scaffold passing through the pore.

In one set of experiments, we used a 16-18 nm diameter pore formed in a 30 nm thick SiN membrane, applying 180 mV in 1M KCl at pH 8. In separate control experiments, unbound 5.6 kb dsDNA scaffold generates a majority of events in the range 100-400 pA and 30-500 microseconds. Also, free RecA events are 100-600 pA, 20-200 usec. Finally, RecA-bound DNA events are typically much deeper blockades, in the range 0.5-3 nA, and with longer duration (0.2-3 milliseconds). Representative events for RecA-bound DNA are shown in FIG. 10 and FIG. 11. These events have interesting patterns, which in the paper by Kowalczyk et al. ["Detection of local protein structures along DNA using solid-state nanopores." *Nano letters* 10, no. 1 (2009): 324-328] the authors attempt to infer the location and length of RecA filaments that are bound to each DNA; however, this is speculative, since it assumes a uniform passage rate through the pore even though another study showed that dsDNA does not pass through a pore at a uniform rate [Lu, Bo, et al. "Origins and consequences of velocity fluctuations during DNA passage through a nanopore." *Biophysical journal* 101.1 (2011): 70-79]. FIGS. 12A and C show the event plot for 1385 events recorded over 10 minutes. Note that amplitude is normalized by voltage to give event conductance values, which is common in nanopore research papers. For example, a mean conductance of 14 nS at 200 mV is equivalent to a mean current amplitude of 2.8 nA. Observe that there are two apparent sub-populations in amplitude (or equivalently, conductance) and duration, with the deeper and longer duration events attributable to RecA-bound DNA. Looking at the maximum current shift value (FIGS. 12A-12B) instead of the mean (FIGS. 12C-12D) makes the subpopulations events more distinct. Note that RecA-bound DNA vs. unbound DNA event patterns are consistent with the model signal patterns in FIG. 3A.

In separate experiments, to further aid in detection, RecA antibody can be used to bind to RecA-bound DNA molecules; this adds a feature to the RecA-DNA molecules that can further attenuate the current amplitude and thereby creating an event type that is even easier to distinguish from unbound DNA and implies that the model protein (RecA in this case) is bound to DNA for these event types. The DNA/RecA reagent binds antibody biomarker creating a DNA/RecA/Ab complex by incubating one nanomolar DNA/RecA for 30 mins with an anti-RecA monoclonal antibody (ARM191, Fisher Scientific) at a 1:10000 dilution. Electrophoretic mobility shift assays, 5% TBE polyacrylamide gel in 1×TBE buffer, are used to test the DNA/RecA and DNA/RecA/Ab complexes by comparing migration of complexes to DNA only or the proper controls.

Figure 13C:
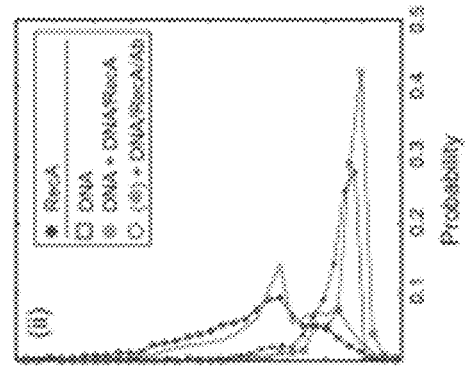
FIGS. 13A-13C illustrate results from a nanopore device detecting DNA/RecA complexes and RecA-antibody on DNA/RecA complexes, the results differentiating these complexes from unbound DNA and also from free RecA.
Figure 13B:
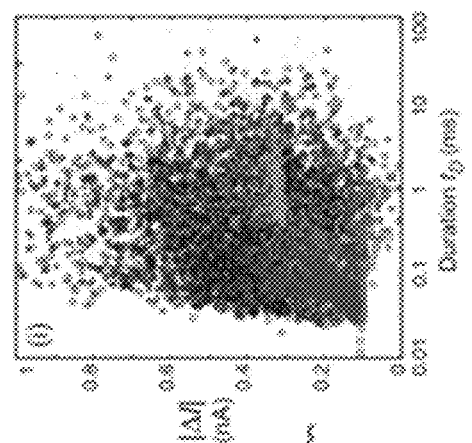
Figure 13A:
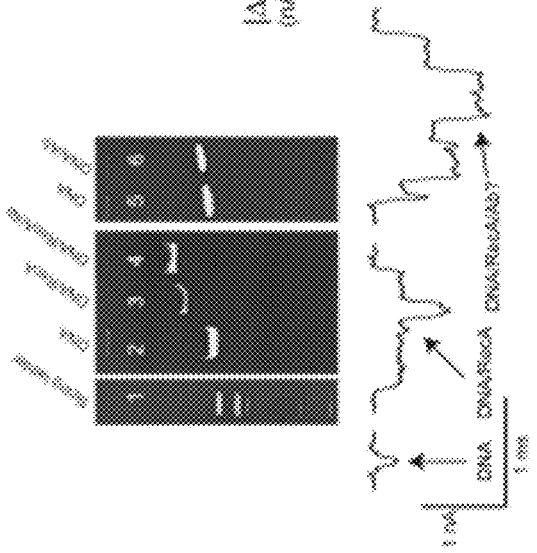

The nanopore experiments were run at 200 mV in 1M LiCl with a pore that varied in diameter: 20 nm during the DNA alone control, and then enlarged to 27 nm after RecA-bound DNA complexes were added. In a gel shift experiment, FIG. 13A shows a clear shift for DNA/RecA/mAb above DNA/RecA, which is in turn well above the unbound 5.6 kb dsDNA scaffold. This complex was tested experimentally with a nanopore. Specifically, 0.1 nM DNA was added to the chamber above the pore, and after 10 minutes of recording 1.25 nM DNA/RecA was added. After another period of recording, 1.25 nM DNA/RecA/mAb was added. With the AB-bound complexes in solution, a new multi-level event type was observed (FIG. 13B) that did not match event patterns characteristic of the other two complex types (DNA, DNA/RecA). The $\Delta l$ vs. $t_D$ distributions of events recorded during each phase of the experiment (FIG. 13C) show that RecA-bound DNA events have longer durations $t_D$, and 3 times as many events had a mean amplitude shift $\Delta l$ greater than 0.6 nA after DNA/RecA/mAb was added. A simple criteria for tagging events in this data set as also being Ab-bound is $(\Delta l, t_D) > (0.6 \text{ nA}, 0.2 \text{ ms})$. Identifying a best signature that is almost absent in unbound DNA type events, but is present in a significant fraction of RecA-bound events (with or without Ab also bound to DNA/RecA), is useful for detection of the presence of RecA-bound DNA complexes in solution above the nanopore.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for determining a presence or an absence of a target protein in a biological sample, comprising the steps of:
    (a) providing a dsDNA synthetically modified to comprise a plurality of target protein binding sites, wherein each target protein binding site of the plurality of target protein binding sites:
        (i) comprises a 5 base pair (bp) to 30 bp polynucleotide having a specific affinity to the target protein,
        (ii) is capable of binding to no more than one target protein,
        (iii) is spaced apart from any other target protein binding site, and
        (iv) is flanked by two polynucleotides, wherein the two polynucleotides flanking the target protein binding site are non-binding sites that do not bind to the target protein, such that the two polynucleotides inhibit non-specific binding of the target protein in the biological sample to the synthetically modified dsDNA;
    (b) contacting the biological sample with the synthetically modified dsDNA under a condition allowing the target protein, if present, to bind to at least one target protein binding site on the synthetically modified dsDNA;
    (c) loading the synthetically modified dsDNA into a single nanopore device comprising a silicon nitride substrate of a thickness ranging between 5 nm and 100 nm, wherein said single nanopore device comprises a nanopore having a diameter of no more than 100 nm and a depth of no more than 100 nm, a first chamber, and a second chamber, wherein each of the first chamber and the second chamber comprises a buffer, wherein the first chamber and the second chamber are in fluid communication through the nanopore, and wherein the single nanopore device comprises a sensitive voltage-clamp amplifier;
    (d) applying a voltage across the nanopore to pass the synthetically modified dsDNA through said nanopore from the first chamber to the second chamber; collecting an electrical signal from the sensitive voltage-clamp amplifier, wherein the electrical signal is correlated with translocation of the synthetically modified dsDNA through the nanopore;
    (e) comparing the electrical signal with a reference electrical signal through an open pore thereby detecting a change in the electrical signal; and
    (g) determining from the change in the electrical signal whether the synthetically modified dsDNA is bound to the target protein, wherein the change in the electrical signal indicates whether or not the synthetically modified dsDNA is bound to the target protein.

2. The method of claim 1, wherein the plurality of target protein binding sites comprises at least three target protein binding sites including a first target protein binding site, a second target protein binding site and a third target protein binding site.

3. The method of claim 2, wherein the second target protein binding site comprises a nucleotide sequence that is different from the nucleotide sequence of the first target protein binding site.

4. The method of claim 2, wherein the third target protein binding site comprises a nucleotide sequence that is identical to the nucleotide sequence of the first target protein binding site.

5. The method of claim 1, wherein said target protein is a mammalian protein.

6. The method of claim 5, wherein the mammalian protein is selected from the group consisting of an antibody, an epitope, a hormone, a neurotransmitter, a cytokine, a growth factor, a cell recognition molecule, and a receptor.

7. The method of claim 2, wherein the synthetically modified dsDNA comprises a spacer polynucleotide of 100 base pairs (bp) to 1000 bp between the first target protein binding site and the second target protein binding site.

8. The method of claim 1, wherein each binding site of the plurality of target protein binding sites is less than 20 base pair sequence.

* * * * *